(12) United States Patent
Gioeli

(10) Patent No.: US 11,788,091 B2
(45) Date of Patent: Oct. 17, 2023

(54) METHODS AND COMPOSITIONS FOR DIAGNOSING AND TREATING PROSTATE CANCER BASED ON LONG NONCODING RNA OVERLAPPING THE LCK GENE THAT REGULATES PROSTATE CANCER CELL GROWTH

(71) Applicant: University of Virginia Patent Foundation, Charlottesville, VA (US)

(72) Inventor: Daniel G. Gioeli, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 55 days.

(21) Appl. No.: 16/999,959

(22) Filed: Aug. 21, 2020

(65) Prior Publication Data

US 2021/0054382 A1 Feb. 25, 2021

Related U.S. Application Data

(60) Provisional application No. 62/889,705, filed on Aug. 21, 2019.

(51) Int. Cl.
*C12Q 1/6886* (2018.01)
*C12N 15/113* (2010.01)

(52) U.S. Cl.
CPC ........ *C12N 15/1137* (2013.01); *C12Q 1/6886* (2013.01); *C12N 2310/14* (2013.01); *C12N 2310/531* (2013.01); *C12Q 2600/158* (2013.01)

(58) Field of Classification Search
CPC .................................................. C12N 15/1137
USPC ...................................................... 424/130.1
See application file for complete search history.

(56) References Cited

U.S. PATENT DOCUMENTS

| | | |
|---|---|---|
| 4,235,871 A | 11/1980 | Papahadjopoulos et al. |
| 4,551,482 A | 11/1985 | Tschang et al. |
| 4,683,195 A | 7/1987 | Mullis et al. |
| 4,683,202 A | 7/1987 | Mullis |
| 5,011,634 A | 4/1991 | Pietsch et al. |
| 5,490,840 A | 2/1996 | Uzgiris et al. |
| 5,510,103 A | 4/1996 | Yokoyama et al. |
| 5,651,991 A | 7/1997 | Sugiyama et al. |
| 5,688,931 A | 11/1997 | Nogusa et al. |
| 5,714,166 A | 2/1998 | Tomalia et al. |
| 5,786,387 A | 7/1998 | Watanabe et al. |
| 5,855,900 A | 1/1999 | Nobuhiko |
| 5,858,410 A | 1/1999 | Muller et al. |
| 5,922,356 A | 7/1999 | Koseki et al. |
| 5,922,545 A | 7/1999 | Mattheakis et al. |
| 5,948,767 A | 9/1999 | Scheule et al. |
| 5,994,392 A | 11/1999 | Shashoua |
| 6,056,938 A | 5/2000 | Unger et al. |
| 6,106,866 A | 8/2000 | Ranney |
| 6,132,766 A | 10/2000 | Sankaram et al. |
| 6,197,333 B1 | 3/2001 | Onyuksel et al. |
| 6,200,598 B1 | 3/2001 | Needham |
| 6,210,707 B1 | 4/2001 | Papahadjopoulos |
| 6,217,886 B1 | 4/2001 | Onyuksel et al. |
| 2005/0019927 A1* | 1/2005 | Hildinger ............... C12N 15/86 435/456 |
| 2010/0120788 A1* | 5/2010 | Wang ................... C12Q 1/6886 435/7.1 |
| 2010/0129804 A1 | 5/2010 | Chinnaiyan et al. |
| 2021/0071268 A1 | 3/2021 | Gioli |

FOREIGN PATENT DOCUMENTS

| | | |
|---|---|---|
| WO | WO 2019/005754 A1 * | 1/2019 |
| WO | WO 2022/103988 A2 | 5/2022 |

OTHER PUBLICATIONS

Tockman et al (Cancer Res., 1992, 52:2711s-2718s).*
Zhang et al (Int J Clin Exp, 2015, (8)(9): 15146-15154).*
Ta et al (Cancer Research, 2016, 76(14_Supplement), Abstract979).*
Cheng et al (Cancer Research, 2006, 66(21): 10613-10620).*
Hu et al. (EMBO reports, 2012, 13(11): 971-983).*
Clarke-Pearson et al (NEJM, 2009, 361: 170-177).*
Park et al (Cancer Investigation, 2016, 34(10): 517-520).*
Abeshouse et al., "The Molecular Taxonomy of Primary Prostate Cancer." Cell, vol. 163(4), pp. 1011-1025 (2015).
Akhade et al., "Long Noncoding RNA: Genome Organization and Mechanism of Action." In: Advances in experimental medicine and biology, pp. 47-74 (2017).
Alexander et al., "Annotating non-coding regions of the genome." Nat Rev Genet, vol. 11(8), pp. 559-571 (2010).
Asangani et al., "Therapeutic targeting of BET bromodomain proteins in castration-resistant prostate cancer." Nature, vol. 510, pp. 278-282 (2014).
Balbin et al., "The landscape of antisense gene expression in human cancers." Genome Res, vol. 25(7), pp. 1068-1079 (2015).
Barton et al., "Multiple molecular subtypes of triple-negative breast cancer critically rely on androgen receptor and respond to enzalutamide in vivo." Mol Cancer Ther, vol. 14(3), pp. 769-778 (2015).
Benayoun et al., "H3K4me3 Breadth Is Linked to Cell Identity and Transcriptional Consistency." Cell, vol. 163(5), pp. 1281-1286 (2015).
Betageri et al., Liposome Drug Delivery Systems, Technomic Publishing, Lancaster, 1993.
Brunner et al., "Transcriptional profiling of long non-coding RNAs and novel transcribed regions across a diverse panel of archived human cancers." Genome Biol, vol. 13(8), p. R75 (2012).

(Continued)

*Primary Examiner* — Sean E Aeder
(74) *Attorney, Agent, or Firm* — Jenkins, Taylor & Hunt, P.A.

(57) ABSTRACT

Provided herein is a previously unannotated lncRNA lying within exon six and 3'UTR of the LCK gene, labeled "HULLK" for Hormone-Upregulated lncRNA within LCK. HULLK is a novel lncRNA situated within the LCK gene that can serve as an oncogene in PCa. Accordingly, provided are methods and compositions for diagnosing and treating prostate cancer based on HULLK that regulates prostate cancer cell growth.

22 Claims, 14 Drawing Sheets

Specification includes a Sequence Listing.

(56) References Cited

OTHER PUBLICATIONS

Buie et al., "Self-complementary AAV Virus (scAAV) Safe and Long-term Gene Transfer in the Trabecular Meshwork of Living Rats and Monkeys." Invest Ophthalmol Vis Sci, vol. 51, pp. 236-248 (2010).
Chakravarty et al., "The oestrogen receptor alpha-regulated lncRNA NEAT1 is a critical modulator of prostate cancer." Nat Commun, vol. 5, p. 5383 (2014).
Clemson et al., "An architectural role for a nuclear noncoding RNA: NEAT1 RNA is essential for the structure of paraspeckles." Mol Cell, vol. 33(6), pp. 717-726 (2009).
Debes et al., "The role of androgens and the androgen receptor in prostate cancer." Cancer Lett, vol. 187, pp. 1-7 (2002).
Derrien et al., "The GENCODE v7 catalog of human long noncoding RNAs: Analysis of their gene structure, evolution, and expression." Genome Res, vol. 22(9), pp. 1775-1789 (2012).
ENCODE Project Consortium. "An integrated encyclopedia of DNA elements in the human genome." Nature, vol. 489, pp. 57-74 (2012).
Fu et al., "p300 and p300/cAMP-response element-binding protein-associated factor acetylate the androgen receptor at sites governing hormone-dependent transactivation." J Biol Chem, vol. 275(27), pp. 20853-20860 (2000).
Geisler et al., "RNA in unexpected places: long non-coding RNA functions in diverse cellular contexts." Nat Rev Mol Cell Biol, vol. 14(11), pp. 699-712 (2013).
Giaccia et al., "The complexity of p53 modulation: emerging patterns from divergent signals." Genes Dev, vol. 12(19), pp. 2973-2983 (1998).
Goldman et al., "Targeted Gene Delivery to Kaposi's Sarcoma Cells via the Fibroblast Growth Factor Receptor." Cancer Res, vol. 57, pp. 1447-1451 (1997).
Goldman et al., "In vitro and in vivo gene delivery mediated by a synthetic polycationic amino polymer." Nat Biotechnol, vol. 15, pp. 462-466 (1997).
Gordon et al., "CDK9 regulates AR promoter selectivity and cell growth through serine 81 phosphorylation." Mol Endochrinol, vol. 24(12), pp. 2267-2280 (2010).
Harris et al., "Ubiquitin-mediated degradation of active Src tyrosine kinase." Proc Natl Acad Sci USA, vol. 96(24), pp. 13738-13743 (1999).
Heemers et al., "Androgen Receptor (AR) Coregulators: A Diversity of Functions Converging on and Regulating the AR Transcriptional Complex." Endocr Rev, vol. 28(7), pp. 778-808 (2007).
Heer et al., "The role of androgen in determining differentiation and regulation of androgen receptor expression in the human prostatic epithelium transient amplifying population." J Cell Physiol, vol. 212(3), pp. 572-578 (2007).
Heller et al., "In vivo gene electroinjection and expression in rat liver." FEBS Lett, vol. 389, pp. 225-228 (1996).
Holliday et al., "Choosing the right cell line for breast cancer research." Breast Cancer Res, vol. 13(4), p. 215 (2011).
Hurley et al., "ATM and ATR: components of an integrated circuit." Cell Cycle, vol. 6(4), 414-417 (2007).
Hutchinson et al., "A screen for nuclear transcripts identifies two linked noncoding RNAs associated with SC35 splicing domains." BMC Genomics, vol. 8(8) (2007).
Innis et al., PCR protocols: a guide to method and applications. Academic Press Incorporated 1990.
Jia et al., "Long noncoding RNA DANCR promotes invasion of prostate cancer through epigenetically silencing expression of TIMP2/3." Oncotarget, vol. 7(25), pp. 37868-37881 (2014).
Kretz et al., "Suppression of progenitor differentiation requires the long noncoding RNA ANCR." Genes Dev, vol. 26(4), pp. 338-343 (2012).
Lee, "Epigenetic Regulation by Long Noncoding RNAs." Science, vol. 338, pp. 1435-1439 (2012).
Lemos et al., "PCA3 long noncoding RNA modulates the expression of key cancer-related genes in LNCaP prostate cancer cells." Tumor Biol, vol. 37(8), pp. 11339-11348 (2016).
Lizio et al., "Gateways to the FANTOM5 promoter level mammalian expression atlas." Genome Biol, vol. 16(1), p. 22 (2015).
Ma et al., "Androgen receptor enhances cell adhesion and decreases cell migration via modulating β-integrin-AKT signaling in hepatocellular carcinoma cells." Cancer Lett, vol. 351(1), pp. 64-71 (2014).
Macedo et al., "Role of Androgens on MCF-7 Breast Cancer Cell Growth and on the Inhibitory Effect of Letrozole." Cancer Res, vol. 66(15), pp. 7775-7782 (2006).
Magnaghi-Jaulin et al., "Retinoblastoma protein represses transcription by recruiting a histone deacetylase." Nature, vol. 391, pp. 601-605 (1998).
Malik et al., "The lncRNA PCAT29 Inhibits Oncogenic Phenotypes in Prostate Cancer." Mol Cancer Res, vol. 12(8), pp. 1081-1087 (2014).
Manome et al., "Enhancer Sequences of the DF3 Gene Regulate Expression of the Herpes Simplex Virus Thymidine Kinase Gene and Confer Sensitivity of Human Breast Cancer Cells to Ganciclovir." Cancer Res, vol. 54, pp. 5408-5413 (1994).
Miklavcic et al., "The Importance of Electric Field Distribution for Effective in Vivo Electroporation of Tissues." Biophys J, vol. 74, pp. 2152-2158 (1998).
Necsulea et al., "The evolution of lncRNA repertoires and expression patterns in tetrapods." Nature, vol. 505, pp. 635-640 (2014).
Ning et al., "The Evolution and Expression Pattern of Human Overlapping lncRNA and Protein-coding Gene Pairs." Sci Rep, vol. 7(1), Article No. 42775 (2017).
Oda et al., "Regulation of the Src family tyrosine kinase Blk through E6AP-mediated ubiquitination." Proc Natl Acad Sci USA, vol. 96(17), pp. 9557-9562 (1999).
Parolia et al., "The long non-coding RNA PCGEM1 is regulated by androgen receptor activity in vivo." Mol Cancer, vol. 14, p. 46 (2015).
Prensner et al., "The long non-coding RNA PCAT-1 promotes prostate cancer cell proliferation through cMyc." Neoplasia, vol. 16(11), pp. 900-908 (2014).
Prensner et al., "The long noncoding RNA SChLAPI promotes aggressive prostate cancer and antagonizes the SWI/SNF complex." Nat Genet, vol. 45(11), pp. 1392-1398 (2013).
Presner et al., "The emergence of lncRNAs in cancer biology." Cancer Discov, vol. 1(5), pp. 391-407 (2011).
Radestad et al., "Characterization of infiltrating lymphocytes in human benign and malignant prostate tissue." Oncotarget, vol. 8(36), pp. 60257-60269 (2017).
Rao et al., "Negative regulation of LCk by Cbl ubiquitin ligase." Proc Natl Acad Sci USA, vol. 99(6), pp. 3794-3799 (2002).
Salameh et al., "PRUNE2 is a human prostate cancer suppressor regulated by the intronic long noncoding RNA PCA3." Proc Natl Acad Sci, vol. 112(27), pp. 8403-8408 (2015).
Fung et al., "Polymeric implants for cancer chemotherapy." Adv Drug Deliv Rev, vol. 26, pp. 209-230 (1997).
Sun et al., "TSVdb: a web-tool for TCGA splicing variants analysis." BMC Genomics, vol. 19(1), p. 405 (2018).
Ta et al., "Discovery of a novel long noncoding RNA overlapping the LCK gene that regulates prostate cancer cell growth." Molecular Cancer, vol. 188, Article No. 113 (2019).
Takayama et al., "Androgen-responsive long noncoding RNA CTBP1-AS promotes prostate cancer." EMBO J, vol. 32(12), pp. 1665-1680 (2013).
Van Heesch et al., "Extensive localization of long noncoding RNAs to the cytosol and mono- and polyribosomal complexes." Genome Biol, vol. 15(1), p. R6 (2014).
Vicat et al., "Brief Report: Muscle Transfection by Electroporation with High-Voltage and Short-Pulse Currents Provides High-Level and Long-Lasting Gene Expression." Hum Gene Ther, vol. 11, pp. 909-916 (2000).
Whitworth et al., "Identification of Kinases Regulating Prostate Cancer Cell Growth Using an RNAi Phenotypic Screen." PLoS One, vol. 7(6), Article ID e38950 (2012).
Xu et al., "Long non-coding RNA ATB promotes growth and epithelial-mesenchymal transition and predicts poor prognosis in human prostate carcinoma." Oncol Rep, vol. 36(1), pp. 10-22 (2016).

(56) References Cited

OTHER PUBLICATIONS

Yang et al., "lncRNA-dependent mechanisms of androgen-receptor-regulated gene activation programs." Nature (2013).
Ylipaa et al., "Transcriptome Sequencing Reveals PCAT5 as a Novel ERG-Regulated Long Noncoding RNA in Prostate Cancer." Cancer Res, vol. 75(19), pp. 4026-4031 (2015).
Zhang et al., "LncRNA HOTAIR Enhances the Androgen-Receptor-Mediated Transcriptional Program and Drives Castration-Resistant Prostate Cancer." Cell Rep, vol. 13(1), pp. 209-221 (2015).
Zhang et al., "Regulation of androgen receptor splice variant AR3 by PCGEM1." Oncatarget, vol. 7(13), pp. 15481-15491 (2016).
Wu et al., "The ligation amplification reaction (LAR)—Amplification of specific DNA sequences using sequential rounds of template-dependent ligation." Genomics, vol. 4, pp. 560-569 (1989).
Altschul et al., "Basic Local Alignment Search Tool," J. Mol. Biol., vol. 215, pp. 403-410 (1990).
Altschul et al., "Protein Database Searches for Multiple Alignments," Proc. Natl. Acad. Sci. USA, vol. 87, pp. 5509-5513 (1990).
International Search Report and Written Opinion corresponding to International Patent Application No. PCT/US2021/059022 dated May 12, 2022.
Needleman & Wunsch, "A General Method Applicable to the Search for Similarities in the Amino Acid Sequence of Two Proteins," J. Mol. Biol., vol. 48, pp. 443-453 (1970).
Ohtsuka et al., "An Alternative Approach to Deoxyoligonucleotides as Hybridization Probes by Insertion of Deoxyinosine at Ambiguous Codon Positions," J. Biol. Chem., vol. 260, No. 5, pp. 2605-2608 (1985).
Pearson & Lipman, "Improved Tools for Biological Sequence Comparison," Proc. Natl. Acad. Sci. USA, vol. 85, pp. 2444-2448 (1988).
Rossolini et al., "Use of Deoxyinosine-Containing Primers vs. Degenerate Primers for Polymerase Chain Reaction Based on Ambiguous Sequence Information," Molecular and Cellular Probes, vol. 8, No. 2, pp. 91-98 (1994).
Smith & Waterman, "Identification of Common Molecular Subsequences," J. Mol. Biol., vol. 147, No. 1, pp. 195-197 (1981).

\* cited by examiner

|  | FFPE | Frozen | Pooled |
|---|---|---|---|
| Slope of line | 0.221 | 0.106 | 0.172 |
| Standard Error | 0.068 | 0.034 | 0.044 |
| p value | 0.003 | 0.008 | <0.001 |
FIG. 4E
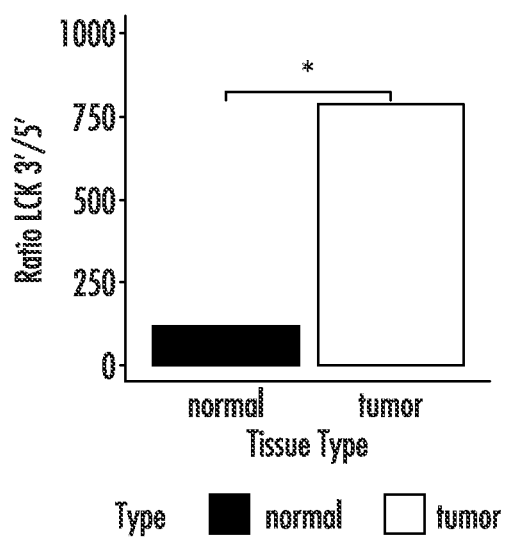
FIG. 4F
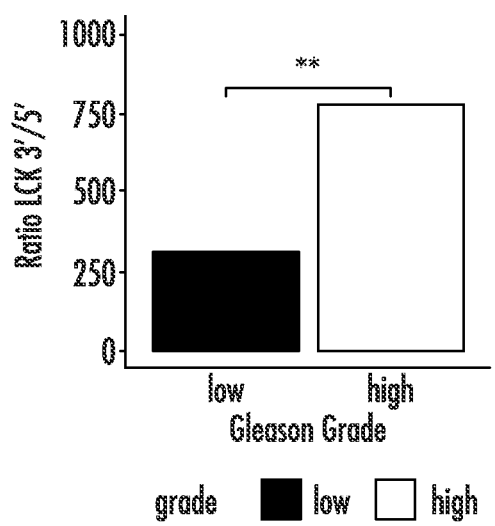
FIG. 4G METHODS AND COMPOSITIONS FOR DIAGNOSING AND TREATING PROSTATE CANCER BASED ON LONG NONCODING RNA OVERLAPPING THE LCK GENE THAT REGULATES PROSTATE CANCER CELL GROWTH

CROSS REFERENCE TO RELATED APPLICATION

The presently disclosed subject matter claims the benefit of U.S. Provisional Patent Application Ser. No. 62/889,705, filed Aug. 21, 2019; the disclosure of which is incorporated herein by reference in its entirety.

STATEMENT OF GOVERNMENT SUPPORT

This invention was made with government support under Grant No. CA178338 awarded by the National Institutes of Health. The government has certain rights in the invention.

TECHNICAL FIELD

The presently disclosed subject matter relates to biomarkers and therapeutic targets of prostate cancer (PCa). In some embodiments, the presently disclosed subject matter relates to a long noncoding RNA (lncRNA) situated in the LCK gene that can serve as an oncogene in PCa.

Abbreviations

PCa: prostate cancer;
CRPC: castration-resistant prostate cancer;
lncRNA: long noncoding RNA;
qPCR: quantitative PCR;
ddPCR: droplet digital PCR;
LCK: lymphocyte-specific protein tyrosine kinase;
HULLK: hormone-upregulated lncRNA within LCK;
TSS: transcriptional start site;
ncRNA: noncoding RNA;
lncRNA-ATB: long noncoding RNA Activated by Transforming Growth Factor-Beta; PRUNE2: prune homolog 2;
DANCR: differentiation antagonizing non-protein coding RNA;
PCAT: prostate cancer-associated transcript;
PCA3: Prostate Cancer Antigen 3;
CTBP1-AS: c-terminal binding protein 1-antisense;
HOTAIR: HOX transcript antisense RNA;
NEAT1: nuclear-enriched abundant transcript 1;
SChLAP1: second chromosome locus associated with prostate-1;
GAS5: growth arrest-specific 5;
TMPRSS2: transmembrane protease, serine 2;
MDM2: mouse double minute 2 homolog;
FANTOM: functional annotation of the mammalian genome;
ENCODE: encyclopedia of DNA elements;
EMT: epithelial-to-mesenchymal transition;
BET: bromodomain and extra-terminal;
RACE: rapid amplification of cDNA ends;
FFPE: formalin-fixed paraffin-embedded;
NP: normal prostate;
BCa: breast cancer;
ADT: androgen deprivation therapy;
shRNA: short-hairpin RNA;
EIF3I: Eukaryotic translation initiation factor 3 subunit I;
HDAC1: histone deacetylase 1

BACKGROUND

One in forty-one men diagnosed with metastatic prostate cancer (PCa) will die from the disease. While androgen deprivation therapy (ADT) is the current initial treatment for advanced PCa, eventually all men diagnosed with PCa will develop incurable castration-resistant prostate cancer (CRPC).

Next-generation sequencing of the PCa transcriptome has uncovered that approximately a quarter of abundant transcripts are long noncoding RNAs (lncRNAs), suggesting that they may play a larger role in PCa than originally thought (1). In fact, PCa-specific lncRNAs have been reported for every stage in the progression of the disease. Therefore, lncRNAs may serve as therapeutic targets for combating PCa progression. Unfortunately, despite the growing list of annotated lncRNAs predicted by RNA sequencing, the number of lncRNAs that have been thoroughly defined and experimentally verified is very small. It is presumable that thousands of lncRNAs remain to be detected since those arising from overlapping protein-coding loci still need to be analyzed (16).

Therefore, there exists a serious need for more effective therapies for the treatment of advanced PCa, and that requires a more complete understanding of PCa development and progression.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this Summary does not list or suggest all possible combinations of such features.

In some embodiments, provided herein are methods of modulating lymphocyte-specific protein tyrosine kinase (LCK) activity in a vertebrate subject. The methods can in some embodiments comprise administering to the vertebrate subject an effective amount of a substance capable of modulating expression of an LCK gene in the vertebrate subject, wherein the substance comprises an RNA interference (RNAi) molecule directed to the LCK gene, whereby modulation of LCK activity is accomplished. In some embodiments, modulating expression of the LCK gene comprises modulating expression of a long noncoding RNA (lncRNA) of the LCK gene. The lncRNA can comprise a hormone upregulated lncRNA within the LCK gene (HULLK).

In some embodiments, HULLK can comprise a nucleotide sequence having at least about 75% sequence identity to SEQ ID NO. 1. In some aspects, the RNAi molecule comprises a short hairpin RNA (shRNA), whereby the shRNA modulates expression of the LCK gene by RNAi. In some aspects, the shRNA can comprises shLCK-3 and/or shLCK-4. The shRNA can be configured to target a carboxy-terminal of the LCK gene.

In some aspects, the substance further comprises an anti-androgen compound, optionally wherein the anti-androgen compound is selected from the group consisting of enzalutamide, an inhibitor of p300, an inhibitor of the bromodomain family, and an inhibitor of the extra-terminal (BET) family. The substance can further comprise a delivery vehicle, such as but not limited to a viral vector, an antibody, an aptamer or a nanoparticle, for delivering the shRNA to a target cell.

In some aspects, the RNAi molecule can comprise a small interfering RNA (siRNA), whereby the siRNA modulates expression the LCK gene by RNAi. The substance can further comprises a delivery vehicle, wherein the delivery vehicle is selected from a viral vector, an antibody, an aptamer, or a nanoparticle for delivering the siRNA to a target cell. The substance can be configured to target HULLK in cytoplasm of a cell in the vertebrate subject.

In some aspects, modulating expression of the LCK gene can modulate growth and/or proliferation of a prostate cancer (PCa) cell within the vertebrate subject. The vertebrate subject can in some aspects be suffering from PCa, wherein the PCa comprises androgen-dependent PCa and/or castration-resistant PCa.

Also provided herein in some embodiments are compositions for modulating expression of hormone upregulated long noncoding RNA within LCK gene (HULLK), the compositions comprising an RNAi construct configured to modulate expression of HULLK. The RNAi can comprise a siRNA, shRNA, miRNA, or ribozyme. The siRNA, shRNA, miRNA, or ribozyme can be specific for a vertebrate HULLK comprising a nucleotide sequence of SEQ ID NO. 1 or variant thereof, wherein the variant has at least about 75% sequence identity to SEQ ID NO. 1. In some aspects, the compositions can further comprise a pharmaceutically acceptable carrier.

Provided are expression vectors comprising a nucleic acid sequence encoding an RNAi construct as disclosed herein. The expression vector can in some embodiments be a retroviral vector. Mammalian cells comprising such an expression vector are also provided.

In some embodiments, provided herein are methods of diagnosing a cancer in a subject. Such methods can comprise providing a sample from a subject, analyzing the sample with or without prior concentration of the sample to determine the presence of and/or expression level of hormone upregulated long noncoding RNA within LCK gene (HULLK) in the sample, and diagnosing the subject as having a cancer based on the detection of and/or expression level of HULLK in the sample. Diagnosing a cancer can comprise diagnosing a prostate cancer (PCa).

Such methods can in some aspects further comprise determining the presence of cytoplasmic HULLK in a sample from the subject, wherein identifying the presence of cytoplasmic HULLK is indicative of metastatic PCa. In some embodiments, the subject is a human subject suspected of having PCa.

These and other objects are achieved in whole or in part by the presently disclosed subject matter. Further, other objects and advantages of the presently disclosed subject matter will become apparent to those skilled in the art after a study of the following description, Drawings and Examples.

BRIEF DESCRIPTION OF THE DRAWINGS

The presently disclosed subject matter can be better understood by referring to the following figures. The components in the figures are not necessarily to scale, emphasis instead being placed upon illustrating the principles of the presently disclosed subject matter (often schematically). In the figures, like reference numerals designate corresponding parts throughout the different views. A further understanding of the presently disclosed subject matter can be obtained by reference to an embodiment set forth in the illustrations of the accompanying drawings. Although the illustrated embodiment is merely exemplary of systems for carrying out the presently disclosed subject matter, both the organization and method of operation of the presently disclosed subject matter, in general, together with further objectives and advantages thereof, may be more easily understood by reference to the drawings and the following description. The drawings are not intended to limit the scope of this presently disclosed subject matter, which is set forth with particularity in the claims as appended or as subsequently amended, but merely to clarify and exemplify the presently disclosed subject matter. For a more complete understanding of the presently disclosed subject matter, reference is now made to the following drawings in which:

FIG. 1A shows the results of LCK protein expression in PCa cells in response to serum starvation or hormone supplementation. LCK protein was immunoprecipitated from 1 mg cell lysate from LNCaP, C4-2, and Jurkat cells cultured in the appropriate growth media for 48 hrs and treated with 1 nM R1881 or starved of hormone for 24 hrs, separated by 10% SDS-PAGE, and immunoblotted with LCK antibodies targeting the amino- and carboxy-terminals. Representative blots are shown, n=3. FIG. 1B shows results of the inhibition of the proteasome does not reveal LCK protein expression. LNCaP cells were seeded and treated with 10 μM MG132 in the presence or absence of R1881 for the indicated timepoints. Cell lysates were blotted for LCK (c-terminal), LCK (n-terminal), p53, ERK1/2, Ran, and Histone H3. Representative blots are shown, n=3. 5'/3' RACE was performed to determine the sequence of a candidate RNA species as shown in FIG. 1C. Representative gel is shown, n=3. LNCaP cells were grown in the absence or presence of 1 nM R1881 for 24 hrs. RNA was collected using the Qiagen RNeasy kit. 5'/3' RACE identified a candidate lncRNA spanning exon 6 through the 3'UTR of LCK as shown in FIG. 1D.

FIG. 1A shows that HULLK is positively regulated by androgen, n=3. LNCaP and C42 cells were transduced with two independent shRNAs to LCK and treated with 0-1 nM R1881. RNA was collected on Day 4 and LCK transcript levels were determined using LCK primers targeting the 3'UTR. FIG. 2B shows that Enzalutamide blocks the androgen-induced expression of HULLK, n=3. LNCaP and C42 cells were seeded for 48 hrs, and then, treated with 1 nM R1881 in the presence or absence of 10 μM enzalutamide. RNA was collected 24 hrs after treatment and LCK transcript levels were determined by qPCR using LCK primers targeting the 3'UTR. HULLK is not upregulated in AR-null PCa cells, n=3, as shown in FIG. 2C. C4-2, DU145, and PC3 cells were seeded in CSS media for 48 hrs, and then, treated with 1 nM R1881 for 16 hrs. RNA was collected and LCK transcript levels were determined using LCK primers targeting the 3'UTR. In FIG. 2D the data show that inhibition of p300 blocks the increase in HULLK expression induced by hormone, n=3. FIG. 2E illustrates that Brd4 inhibition reduces the hormone induction of HULLK, n=3. LNCaP, C42, or Jurkat cells were seeded for 48 hrs in the appropriate growth media, and then, treated with 1 nM R1881 in the presence or absence of 0.3 μM A-485 or 0.1 μM JQ1. RNA was collected 24 hrs after treatment and LCK transcript levels were determined by qPCR using LCK primers targeting exon 13 or 3'UTR. PSA and TMPRSS2 transcripts were determined to verify the efficacy of p300 and Brd4 inhibition.

As shown in FIG. 3A, HULLK is transcribed from the sense strand of DNA. LNCaP cells were seeded for 48 hrs and treated with 1 nM R1881 for 24 hrs. RNA was collected and cDNA was synthesized using strand-specific primers. qPCR was performed with two independent LCK primer sets that amplify HULLK, n=3. As shown in FIG. 3B, HULLK is localized to the cytoplasm. LNCaP cells were seeded for 48 hrs and treated with 1 nM R1881 for 24 hrs. Whole cell lysates were separated into cytoplasmic and nuclear fractions by centrifugation. RNA was collected from each fraction and cDNA was synthesized using the iScript cDNA synthesis kit. qPCR was performed with two independent LCK primer sets that amplify HULLK, and cytoplasmic and nuclear control genes, n=3.

FIGS. 4A through 4G illustrate that HULLK expression is present in prostate cancer. FIG. 4A shows the expression of HULLK in a panel of PCa and normal prostate epithelial cell lines cultured in complete growth media. qPCR was performed with two independent LCK primer sets targeting exon 2 (E2) and the 3'UTR (3U), n=3. HULLK expression in C4-2, MCF7, BT549, MDA-MB-231, HeLa, and PANC1 cell lines grown in complete growth media is shown in FIG. 4B. qPCR was performed with LCK primers targeting the 3'UTR, n=3. The data plotted in FIG. 4C shows a significant positive correlation between HULLK expression and PCa grade. 33 FFPE tissue samples were obtained from the Biorepository and Tissue Research Facility at the University of Virginia. These samples represent biopsies and surgical resections collected in 2016 from PCa patients presenting with Gleason Score 6-10. Normal and cancerous regions were demarcated and 1.5 mm punches were collected. ddPCR was performed on the QX200 droplet digital PCR system (Bio-Rad). The data plotted in FIG. 4D is based on 16 fresh-frozen tissue samples from Gleason Score 6-10 PCa patients were acquired from Dr. Ganesh Raj from the University of Texas Southwestern Medical Center. These samples were surgically resected from May to December in 2017, placed in RNALater (ThermoFisher), and frozen immediately. FIG. 4E summarizes the statistical analysis of the association between the LCK E13 to LCK E4 ratio and grade was performed using linear regression models, following transformation to the log scale. The analyses were conducted separately for frozen and FFPE samples, with a test for interaction used to test whether the association between the E13 to E4 ratio and grade was the same in frozen samples as in FFPE samples. (F) HULLK expression in normal and tumor (FIG. 4F) and low Gleason [scores 6 and 7(3+4)] and high Gleason score [scores 7(4+3), and 8-10] (FIG. 4G) in the PRAD TCGA cohort.

FIG. 5A illustrates the gene structure of LCK and location of each shRNA targeting LCK. The percent knockdown of HULLK or LCK message, n=3, is shown in FIG. 5B. MISSION shRNAs targeting human LCK (NM_005356) and the pLKO vector control were purchased from ThermoFisher. Each shRNA was validated for efficiency of LCK or HULLK knockdown in Jurkat and PCa cells by qPCR. (C) The results of CyQuant Assay measuring DNA content as a surrogate for cell number 7 days after shRNA transduction is shown in FIG. 5C. Growth was compared to untreated empty vector control and the values were averaged across biological replicates. Error bars represent standard error of the mean. The relative effect of four independent shRNAs on cell growth in LNCaP, C42, and Rv1 cells in the absence or presence of 0.05 nM R1881, n=3. FIG. 5D plots the data for the relative effect of HULLK overexpression on cell growth in LNCaP, C42, and Rv1 cells in the absence or presence of 0.05 nM R1881, n=3. Statistical analysis was performed using ANOVA and Tukey test.

FIG. 6A shows the expression of AR following HULLK knockdown. LNCaP and C4-2 cells were transduced with vector, shLCK (n-term), or shLCK (c-term) in the appropriate growth media, and whole cell lysates were collected 48 hrs later and blotted for AR21 and ERK1/2, n=3. FIG. 6B shows the expression of AR following HULLK overexpression. LNCaP and C4-2 cells were transduced with vector or HULLK in the appropriate growth media, and whole cell lysates were collected 48 hrs later and blotted for AR21 and α-tubulin, n=3. RNA was collected and AR transcript levels were determined using AR primers targeting the DNA binding domain, n=3.

FIG. 7A shows the expression of AR in breast cancer cell lines. LNCaP, MCF7, BT549, and MDA-MD-231 cells were seeded in the appropriate growth media, and whole cell lysates were collected 48 hrs later and blotted for AR21 and ERK1/2. FIG. 7B shows HULLK expression increases in response to hormone. MCF7, BT549, and MDA-MB-231 cells were seeded in CSS media for 48 hrs, and then, treated with 1 nM R1881 for 16 hrs. RNA was collected and LCK transcript levels were determined using LCK primers targeting the 3'UTR, n=3.

DETAILED DESCRIPTION

Figure 1A:
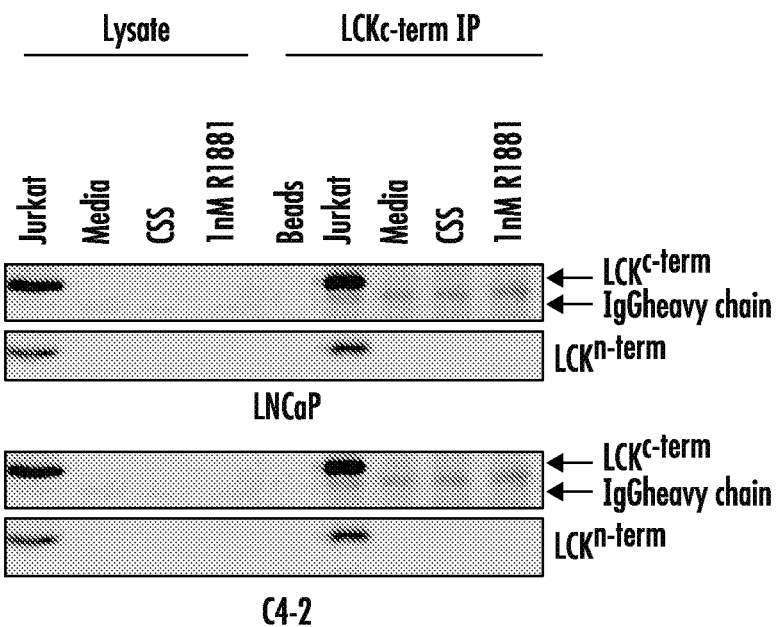
FIGS. 1A to 1D illustrate the discovery of a novel lncRNA in prostate cancer cells.

The presently disclosed subject matter now will be described more fully hereinafter, in which some, but not all embodiments of the presently disclosed subject matter are described. Indeed, the presently disclosed subject matter can be embodied in many different forms and should not be construed as limited to the embodiments set forth herein; rather, these embodiments are provided so that this disclosure will satisfy applicable legal requirements.

I. Definitions

The terminology used herein is for the purpose of describing particular embodiments only and is not intended to be limiting of the presently disclosed subject matter.

While the following terms are believed to be well understood by one of ordinary skill in the art, the following definitions are set forth to facilitate explanation of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art.

Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of a composition, dose, sequence identity (e.g., when comparing two or more nucleotide or amino acid sequences), mass, weight, temperature, time, volume, concentration, percentage, etc., is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

The term "comprising", which is synonymous with "including" "containing" or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

As used herein, the term "and/or" when used in the context of a listing of entities, refers to the entities being present singly or in combination. Thus, for example, the phrase "A, B, C, and/or D" includes A, B, C, and D individually, but also includes any and all combinations and subcombinations of A, B, C, and D.

The term "gene" refers broadly to any segment of DNA associated with a biological function. A gene can comprise sequences including but not limited to a coding sequence, a promoter region, a cis-regulatory sequence, a non-expressed DNA segment that is a specific recognition sequence for regulatory proteins, a non-expressed DNA segment that contributes to gene expression, a DNA segment designed to have desired parameters, or combinations thereof. A gene can be obtained by a variety of methods, including cloning from a biological sample, synthesis based on known or predicted sequence information, and recombinant derivation of an existing sequence.

The terms "modulate" or "alter" are used interchangeably and refer to a change in the expression level of a gene, or a level of RNA molecule or equivalent RNA molecules encoding one or more proteins or protein subunits, or activity of one or more proteins or protein subunits is up regulated or down regulated, such that expression, level, or activity is greater than or less than that observed in the absence of the modulator. For example, the terms "modulate" and/or "alter" can mean "inhibit" or "suppress", but the use of the words "modulate" and/or "alter" are not limited to this definition.

As used herein, the terms "inhibit", "suppress", "repress", "downregulate", "loss of function", "block of function", and grammatical variants thereof are used interchangeably and refer to an activity whereby gene expression (e.g., a level of an RNA encoding one or more gene products) is reduced below that observed in the absence of a composition of the presently disclosed subject matter. In some embodiments, inhibition results in a decrease in the steady state level of a target RNA.

The term "RNA" refers to a molecule comprising at least one ribonucleotide residue. By "ribonucleotide" is meant a nucleotide with a hydroxyl group at the 2' position of a D-ribofuranose moiety. The terms encompass double stranded RNA, single stranded RNA, RNAs with both double stranded and single stranded regions, isolated RNA such as partially purified RNA, essentially pure RNA, synthetic RNA, recombinantly produced RNA, as well as altered RNA, or analog RNA, that differs from naturally occurring RNA by the addition, deletion, substitution, and/or alteration of one or more nucleotides. Such alterations can include addition of non-nucleotide material, for example at one or more nucleotides of the RNA. Nucleotides in the RNA molecules of the presently disclosed subject matter can also comprise non-standard nucleotides, such as non-naturally occurring nucleotides or chemically synthesized nucleotides or deoxynucleotides. These altered RNAs can be referred to as analogs or analogs of a naturally occurring RNA.

The term "promoter" defines a region within a gene that is positioned 5' to a coding region of a same gene and functions to direct transcription of the coding region. The promoter region includes a transcriptional start site and at least one cis-regulatory element. The term "promoter" also includes functional portions of a promoter region, wherein the functional portion is sufficient for gene transcription. To determine nucleotide sequences that are functional, the expression of a reporter gene is assayed when variably placed under the direction of a promoter region fragment.

The terms "active", "functional" and "physiological", as used for example in "enzymatically active", "functional chromatin" and "physiologically accurate", and variations thereof, refer to the states of genes, regulatory components, chromatin, etc. that are reflective of the dynamic states of each as they exists naturally, or in vivo, in contrast to static or non-active states of each. Measurements, detections or screenings based on the active, functional and/or physiologically relevant states of biological indicators can be useful in elucidating a mechanism, or defining a disease state or phenotype, as it occurs naturally. This is in contrast to measurements taken based on static concentrations or quantities of a biological indicator that are not reflective of level of activity or function thereof.

II. Methods and Compositions for Diagnosing and Treating Metastatic Prostate Cancer Virtually all patients with metastatic prostate cancer (PCa) will relapse and develop lethal castration-resistant prostate cancer (CRPC). Next-generation sequencing of the PCa transcriptome has uncovered that approximately a quarter of abundant transcripts are long noncoding RNAs (lncRNAs), suggesting that they may play a role in PCa. PCa-specific lncRNAs may be involved in some or all stages in the progression of the disease. Therefore, lncRNAs may serve as therapeutic targets for combating PCa progression.

In hormone-sensitive PCa, long noncoding RNA Activated by Transforming Growth Factor-Beta (lncRNA-ATB) upregulates the expression of epithelial-to-mesenchymal transition (EMT) factors, which is an important component that promotes CRPC (2). Furthermore, lncRNA-ATB overexpression increases proliferation through the elevation in cyclin D1 and cyclin E. In addition to playing a role in EMT, Prostate Cancer Antigen 3 (PCA3) modulates the expression of several cancer-related genes (vascular endothelial growth factor A, receptor tyrosine-protein kinase, Bcl-2-associated death promoter, and telomerase reverse transcriptase) and androgen receptor (AR) cofactors (3). PCA3 also regulates tumor suppressor prune homolog 2 (PRUNE2) expression by forming a PRUNE2/PCA3 double-stranded RNA complex which results in PRUNE2 translational repression (4). The lncRNA Differentiation Antagonizing Non-Protein Coding RNA (DANCR) has been shown to counter the actions of the androgen-AR signaling axis (5), which drives epithelial cell terminal differentiation in the normal prostate (6) and inhibits invasion and metastasis in PCa (7). Probably functioning as a scaffold, DANCR suppresses differentiation and promotes invasion and metastasis by negatively regulating tissue inhibitor of metalloproteinases 2/3 (TIMP 2/3) expression through enhancer of zeste homolog 2 recruitment (8). The androgen-AR signaling pathway is also opposed by Prostate Cancer-Associated Transcript 29 (PCAT29), which inhibits proliferation and is repressed by the AR (9). Thus, PCa progression may be driven by these lncRNAs at the hormone-sensitive stage of the disease.

During androgen deprivation therapy (ADT), there are two lncRNAs that have been reported to be overexpressed and promote progression to CRPC. Prostate Cancer Gene Expression Marker 1, elevated in response to ADT, translocates to the nucleus and binds U2 small nuclear RNA auxiliary factor 2 and heterogeneous nuclear ribonucleoprotein A1. This results in the upregulation of AR splice variant 7 (AR-V7), and ultimately, induces proliferation (10). C-terminal Binding Protein 1-Antisense (CTBP1-AS) inhibits CTBP1 expression by complexing with the transcriptional repressor Polypyrimidine Tract Binding Protein (PTB)-associating splicing factor (PSF) and recruiting histone decarboxylase (HDAC)-paired amphipathic helix protein Sin3a (Sin3A) complexes to the gene promoter (11). Furthermore, CTBP1-AS promotes cell cycle progression and proliferation through the suppression of p53 and mothers against decapentaplegic homolog 3 expression. Thus, these two lncRNAs may drive CRPC.

While many lncRNAs have been implicated in PCa progression to CRPC, only a small subset has been experimentally validated. For example, the proliferative and invasive capacities of CRPC cells are enhanced as a result of the overexpression of HOX Transcript Antisense RNA (HOTAIR) (12). While the AR usually decreases HOTAIR expression, HOTAIR increases AR activity by preventing ubiquitination and degradation of the AR through the inhibition of mouse double minute 2 homolog (MDM2). The estrogen receptor α (ERα)-regulated lncRNA Nuclear-Enriched Abundant Transcript 1 (NEAT1) not only controls the levels of specific PCa genes, but it also modulates the expression of the Transmembrane Protease, Serine 2 (TMPRSS2)-ERG fusion gene (13). Moreover, ERG-positive CRPC frequently overexpresses PCAT5 (14). Depletion of PCAT5 from PC3 cells diminishes proliferation and invasion and induces apoptosis. Similar to PCAT5, Second Chromosome Locus Associated with Prostate-1 (SChLAP1) also correlates with ERG-positive PCa (15). SChLAP1, which is overexpressed in approximately 25% of all PCa, promotes invasion and migration by interacting with the SWItch/Sucrose Non-Fermentable-complex and blocking its gene expression regulatory function. Despite the growing list of annotated lncRNAs predicted by RNA sequencing, the number of lncRNAs that have been thoroughly defined and experimentally verified is very small. It is presumable that thousands of lncRNAs remain to be detected since those arising from overlapping protein-coding loci still need to be analyzed (16). However, prior to the instant disclosure, no lncRNA suitable for use in treating PCa has been identified.

Disclosed herein is a novel lncRNA encoded within the lymphocyte-specific protein tyrosine kinase (LCK) gene locus in PCa cells. As disclosed herein, this lncRNA is regulated by the AR, as expression was increased in response to hormone and blocked in the presence of enzalutamide, as well as inhibitors of p300 and the bromodomain and extra-terminal (BET) family. As a result, this lncRNA has been labelled "HULLK" for Hormone Upregulated lncRNA within LCK. The polynucleotide sequence of HULLK is provided herein as SEQ ID NO. 1. It is transcribed from the sense strand of DNA and localizes to the cytoplasm. HULLK transcripts are not only expressed in PCa cell lines, but also PCa patient tissue. Furthermore, as disclosed herein, HULLK expression is significantly upregulated with increasing tumor grade. Notably, as demonstrated herein, HULLK knockdown with shRNAs significantly decreases cellular proliferation in the presence and absence of hormone. HULLK overexpression hypersensitizes PCa cells to androgen. Thus, the data included herein indicates that HULLK is a lncRNA situated within the LCK gene that functions as a novel positive regulator of PCa cell growth.

Provided herein are methods of modulating lymphocyte-specific protein tyrosine kinase (LCK) activity in a subject, including for example a vertebrate subject or human subject. Such methods can comprise administering to the vertebrate subject an effective amount of a substance capable of modulating expression of an LCK gene in the vertebrate subject, wherein the substance can comprise an RNA interference (RNAi) molecule directed to the LCK gene, whereby modulation of LCK activity is accomplished. In some aspects, modulating expression of the LCK gene comprises modulating expression of a long noncoding RNA (lncRNA) of the LCK gene. As disclosed herein, the lncRNA can comprise a hormone upregulated lncRNA within the LCK gene (HULLK).

HULLK comprises a nucleotide sequence of SEQ ID NO. 1, or variant thereof. In some embodiments, such variants can have at least about 50%, 60%, 65%, 70%, 75%, 80%, 85%, 90%, 91%, 92%, 93%, 94%, 95%, 96%, 97%, 98%, 99% or 100% sequence identity to SEQ ID NO. 1.

In some embodiments, the RNAi molecule can comprise a short hairpin RNA (shRNA), whereby the shRNA modulates expression of the LCK gene by RNAi. The shRNA comprises shLCK-3 and/or shLCK-4, optionally wherein the shRNA comprises a nucleotide sequence of CCGGGG-GATCCTGCTGACGGAAATTCTCG AGAAT-TTCCGTCAGCAGGATCCCTTTTTG (shLCK-3; SEQ ID NO: 25) and/or CCGGTCACATGGCCTATGCA-CATATCTCGA GATATGTGCATAGGCCATGTGAT-TTTTG (shLCK-4; SEQ ID NO: 26), or variant thereof (50% to 99% sequence identity as defined herein). In some aspects, the shRNA can be configured to target a carboxy-terminal of the LCK gene.

In some aspects, and as discussed further in the Examples, the substance administered to the subject can further comprise an anti-androgen compound, optionally wherein the anti-androgen compound is selected from the group consisting of enzalutamide, an inhibitor of p300, an inhibitor of the bromodomain family, and an inhibitor of the extra-terminal (BET) family. The substance can further comprise a delivery vehicle, such as but not limited to a viral vector, an antibody, an aptamer or a nanoparticle, for delivering the shRNA to a target cell. The RNAi molecule can comprise a small interfering RNA (siRNA), whereby the siRNA modulates expression the LCK gene by RNAi.

In some aspects, the substance administered to the subject can further comprise a delivery vehicle, such as but not limited to a viral vector, an antibody, an aptamer, or a nanoparticle for delivering the siRNA to a target cell. The substance is configured to target HULLK in cytoplasm of a cell in the vertebrate subject.

As discussed herein, by modulating expression of the LCK gene the growth of prostate cancer (PCa) cells or other cancer cells can be modulated in the subject. The vertebrate subject can be any mammal, including a human. The vertebrate subject can be suffering from a form of cancer or related condition or disease, including for example PCa. In some aspects the subject can be suffering from androgen-dependent PCa and/or castration-resistant PCa.

Correspondingly, also provided herein are methods of treating subjects or patients suffering from a cancer, including a prostate cancer (PCa) or related condition. The methods of treatment can comprise providing a subject suffering or believe to be suffering from such a condition and administering to the subject an effective amount of a substance or therapeutic composition capable of modulating expression of an LCK gene in the subject, whereby modulation of the expression of the LCK gene is accomplished. Modulating expression of the LCK gene can modulate growth of PCa cells in the subject.

In such treatment methods the substance or therapeutic composition can comprise an RNA interference (RNAi) molecule directed to the LCK gene, whereby modulation of LCK activity is accomplished. In some aspects, modulating expression of the LCK gene comprises modulating expression of a long noncoding RNA (lncRNA) of the LCK gene. As disclosed herein, the lncRNA can comprise a hormone upregulated lncRNA within the LCK gene (HULLK).

In such treatment or therapeutic methods HULLK can comprise a nucleotide sequence of SEQ ID NO. 1, or variant thereof. In some embodiments, such variants can have at least about 50%, 60%, 65%, 70%, 75%, 80%, 85%, 90%, 91%, 92%, 93%, 94%, 95%, 96%, 97%, 98%, 99% or 100% sequence identity to SEQ ID NO. 1.

In some embodiments of treatment methods the RNAi molecule can comprise a short hairpin RNA (shRNA), whereby the shRNA modulates expression of the LCK gene by RNAi. The shRNA comprises shLCK-3 and/or shLCK-4, optionally wherein the shRNA comprises a nucleotide sequence of SEQ ID NOs: 25 and 26, respectively, or variant thereof (50% to 99% sequence identity as defined herein). In some aspects, the shRNA can be configured to target a carboxy-terminal of the LCK gene.

In some aspects of the therapeutic or treatment methods the substance administered to the subject can further comprise an anti-androgen compound, optionally wherein the anti-androgen compound is selected from the group consisting of enzalutamide, an inhibitor of p300, an inhibitor of the bromodomain family, and an inhibitor of the extra-terminal (BET) family. The substance can further comprise a delivery vehicle, such as but not limited to a viral vector, an antibody, an aptamer or a nanoparticle, for delivering the shRNA to a target cell. The RNAi molecule can comprise a small interfering RNA (siRNA), whereby the siRNA modulates expression the LCK gene by RNAi.

The therapeutic compositions and substances administered to the subject can further comprise a delivery vehicle, such as but not limited to a viral vector, an antibody, an aptamer, or a nanoparticle for delivering the siRNA to a target cell. The substance is configured to target HULLK in cytoplasm of a cell in the vertebrate subject.

As discussed herein, by modulating expression of the LCK gene the growth of prostate cancer (PCa) cells or other cancer cells can be modulated in the subject. The vertebrate subject can be any mammal, including a human. The vertebrate subject can be suffering from a form of cancer or related condition or disease, including for example PCa. In some aspects the subject can be suffering from androgen-dependent PCa and/or castration-resistant PCa. Such methods of treatment can further comprise the administration of radiation therapy, chemotherapy, gene therapy, immunotherapy, a dietary treatment, or combinations thereof.

A method for modulating expression of an LCK gene in a cell, including delivering to the cell an effective amount of a vector comprising a polynucleotide that encodes a siRNA, shRNA, miRNA, or other molecule directed to an LCK gene and/or that interferes with the expression of an LCK gene, or a small molecule, peptide, antibody or aptamer capable of interfering with the LCK gene. Such a method can further comprise maintaining the cell under conditions sufficient for expression of said siRNA, shRNA, miRNA, or a molecule that interferes with the LCK gene by modulating its expression or otherwise interfering with the same. In some aspects, modulating expression of the LCK gene comprises modulating expression of a long noncoding RNA (lncRNA) of the LCK gene, wherein the lncRNA can comprise a hormone upregulated lncRNA within the LCK gene (HULLK). As discussed further herein, HULLK can comprise a nucleotide sequence of SEQ ID NO. 1, or variants thereof. Such methods of modulating gene expression within the cell can include the use of a delivery vehicle, such as but not limited to a viral vector, an aptamer, an antibody or a nanoparticle, for delivering the siRNA, shRNA, and/or miRNA to the cell. The cell can be a PCa cell or other cancer cell where modulating the LCK gene could have a therapeutic effect. In some aspects, the cancer cell can be a primary cancer cell or a cell line representing a primary cancer cell.

Correspondingly, methods are also provided for suppressing the growth of a cancer cell. Such methods can include similar steps and components as that noted hereinabove for modulating expression of an LCK gene in a cell. In such methods, modulating expression of an LCK gene the cancer cell can result in decreased growth of the cancer cell. In such methods, the cell can be in a subject, including a human subject suffering from cancer, including PCa.

In some embodiments compositions for modulating the expression of hormone upregulated long noncoding RNA within LCK gene (HULLK) are also provided. Such compositions can comprise an RNAi construct configured to modulate expression of HULLK. The RNAi can include siRNA, shRNA, miRNA, ribozymes and the like. In some aspects, the siRNA, shRNA, miRNA, or ribozymes can be specific for a vertebrate HULLK comprising a nucleotide sequence of SEQ ID NO. 1 or variant thereof, wherein the variant has at least about 75% sequence identity to SEQ ID NO. 1. As noted herein, such variants can have at least about 50%, 60%, 65%, 70%, 75%, 80%, 85%, 90%, 91%, 92%, 93%, 94%, 95%, 96%, 97%, 98%, 99% or 100% sequence identity to SEQ ID NO. 1. Such compositions can achieve modulation of expression of HULLK in a subject, tissue, cell or sample, including a downregulation in the gene expression of HULLK of about 5%, 10%, 20%, 30%, 40%, 50%, 60%, 70%, 80%, 90%, 95%, 99%, or more.

Also provided are expression vectors comprising a nucleic acid sequence encoding an RNAi construct disclosed herein. Such expression vectors can be inducible and/or responsive to inducers, as discussed further herein. The vectors can be any suitable expression vector, including for example a retroviral vector. Such expression vectors can be within a mammalian cell. Such cells can be a cancer cell, including for example a PCa cell, or other cancer cell where modulating HULLK could have a therapeutic effect.

Pharmaceutical compositions comprising a therapeutically effective amount of a HULLK modulator and a pharmaceutically acceptable diluent or vehicle are provided.

Such compositions can comprise a pharmaceutically acceptable carrier, adjuvant or the like.

In some embodiments, provided herein are methods of diagnosing a cancer in a subject, the methods comprising providing a sample from a subject, analyzing the sample with or without prior concentration of the sample to determine the presence of and/or expression level of hormone upregulated long noncoding RNA within LCK gene (HULLK) in the sample, and diagnosing the subject as having a cancer based on the detection of and/or expression level of HULLK in the sample. Such diagnostic methods can be suitable for diagnosing a prostate cancer (PCa) using HULLK as a biomarker. Such methods can further comprise determining the presence of cytoplasmic HULLK in a sample from the subject, wherein identifying the presence of cytoplasmic HULLK is indicative of metastatic PCa. Such diagnostic methods can be suitable for use with human subjects suspected of having PCa.

```
III. HULLK Polynucleotide Sequence
SEQ ID NO. 1:
      CTGGT TCTTCAAGAA CCTGAGCCGC AAGGACGCGG

AGCGGCAGCT CCTGGCGCCC GGGAACACTC ACGGCTCCTT

CCTCATCCGG GAGAGCGAGA GCACCGCGGG TGAGCGGGCG

GCGGTCTCGA CCGGGCGCGG GGGTGCCCCG GGGTGTGCCC

GAGGGGGGGC GCAGGGTGAG CCCGAGGTGG AGACACGGGG

ATCGTTTTCA CTGTCGGTCC GGGACTTCGA CCAGAACCAG

GGAGAGGTGG TGAAACATTA CAAGATCCGT AATCTGGACA

ACGGTGGCTT CTACATCTCC CCTCGAATCA CTTTTCCCGG

CCTGCATGAA CTGGTCCGCC ATTACACCAA TGCTTCAGAT

CGGGCTGTGC ACACGGTTGA GCCGCCCCTG CAGACCCAGA

AGCCCCAGAA GCCGTGGTGG GAGGACGAGT GGGAGGTTCC

CAGGGAGACG CTGAAGCTGG TGGAGCGGCT GGGGGCTGGA

ACAGTTCGGG GGTGTGGAT GGGGTACTAC AACGGGCACA

CGAAGGTGGC GGTGAAGAGC CTGAAGCAGG GCAGCATGTC

CCCGGACGCC TTCCTGGCCG AGGCCAACCT CATGAAGCAG

CTGCAACACC AGCGGCTGGT TCGGCTCTAC GCTGTGGTCA

CCCAGGAGCC CATCTACATC ATCACTGAAT ACATGGAGAA

TGGGAGTCTA GTGGATTTTC TCAAGACCCC TTCAGGCATC

AAGTTGACCA TCAACAAACT CCTGGACATG GCAGCCCAAA

TTGCAGAAGG CATGGCATTC ATTGAAGAGC GGAATTATAT

TCATCGTGAC CTTCGGGCTG CCAACATTCT GGTGTCTGAC

ACCCTGAGCT GCAAGATTGC AGACTTTGGC CTAGCACGCC

TCATTGAGGA CAACGAGTAC ACAGCCAGGG AGGGGCCAA

GTTTCCCATT AAGTGGACAG CGCCAGAAGC CATTAACTAC

GGGACATTCA CCATCAAGTC AGATGTGTGG TCTTTTGGGA

TCCTGCTGAC GGAAATTGTC ACCCACGGCC GCATCCCTTA

CCCAGGGATG ACCAACCCGG AGGTGATTCA GAACCTGGAG

CGAGGCTACC GCATGGTGCG CCCTGACAAC TGTCCAGAGG

AGCTGTACCA ACTCATGAGG CTGTGCTGGA AGGAGCGCCC

AGAGGACCGG CCCACCTTTG ACTACCTGCG CAGTGTGCTG

GAGGACTTCT TCACGGCCAC AGAGGGCCAG TACCAGCCTC

AGCCTTGAGA GGCCTTGAGA GGCCCTGGGG TTCTCCCCCT

TTCTCTCCAG CCTGACTTGG GGAGATGGAG TTCTTGTGCC

ATAGTCACAT GGCCTATGCA CATATGGACT CTGCACATGA

ATCCCACCCA CATGTGACAC ATATGCACCT TGTGTCTGTA

CACGTGTCCT GTAGTTGCGT GGACTCTGCA CATGTCTTGT

ACATGTGTAG CCTGTGCATG TATGTCTTGG ACACTGTACA

AGGTACCCCT TTCTGGCTCT CCCATTTCCT GAGACCACAG

AGAGAGGGGA GAAGCCTGGG ATTGACAGAA GCTTCTGCCC

ACCTACTTTT CTTTCCTCAG ATCATCCAGA AGTTCCTCAA

GGGCCAGGAC TTTATCTAAT ACCTCTGTGT GCTCCTCCTT

GGTGCCTGGC CTGGCACACA TCAGGAGTTC AATAAATGTC

TGTTGATGAC TGTTGTACA
```

In SEQ ID NO. 1 above, bold text is exon, underlined text is 3'UTR, and regular text is intronic sequence preserved in two 5'RACE clones.

IV. Nucleic Acids

The term "substantially identical", as used herein to describe a degree of similarity between nucleotide sequences, refers to two or more sequences that have in one embodiment at least about least 60%, in another embodiment at least about 70%, in another embodiment at least about 80%, in another embodiment at least about 85%, in another embodiment at least about 90%, in another embodiment at least about 91%, in another embodiment at least about 92%, in another embodiment at least about 93%, in another embodiment at least about 94%, in another embodiment at least about 95%, in another embodiment at least about 96%, in another embodiment at least about 97%, in another embodiment at least about 98%, in another embodiment at least about 99%, in another embodiment about 90% to about 99%, and in another embodiment about 95% to about 99% nucleotide identity, when compared and aligned for maximum correspondence, as measured using one of the following sequence comparison algorithms (described herein below under the heading "Comparison of Nucleotide and Amino Acid Sequences") or by visual inspection. In one embodiment, the substantial identity exists in nucleotide sequences of at least about 100 residues, in another embodiment in nucleotide sequences of at least about 150 residues, and in still another embodiment in nucleotide sequences comprising a full length sequence. The term "full length", as used herein to refer to a complete open reading frame encoding, for example, a gene of interest polypeptide. The term "full length" also encompasses a non-expressed sequence, for example a promoter or an inverted terminal repeat sequence.

In one aspect, polymorphic sequences can be substantially identical sequences. The term "polymorphic" refers to the occurrence of two or more genetically determined alternative sequences or alleles in a population. An allelic difference can be as small as one base pair.

In another aspect, substantially identical sequences can comprise mutagenized sequences, including sequences comprising silent mutations. A mutation can comprise a single base change.

Another indication that two nucleotide sequences are substantially identical is that the two molecules specifically or substantially hybridize to each other under stringent conditions. In the context of nucleic acid hybridization, two nucleic acid sequences being compared can be designated a "probe" and a "target". A "probe" is a reference nucleic acid molecule, and a "target" is a test nucleic acid molecule, often found within a heterogeneous population of nucleic acid molecules. A "target sequence" is synonymous with a "test sequence".

The phrase "hybridizing specifically to" refers to the binding, duplexing, or hybridizing of a molecule only to a particular nucleotide sequence under stringent conditions when that sequence is present in a complex nucleic acid mixture (e.g., total cellular DNA or RNA).

The phrase "hybridizing substantially to" refers to complementary hybridization between a probe nucleic acid molecule and a target nucleic acid molecule and embraces minor mismatches that can be accommodated by reducing the stringency of the hybridization media to achieve the desired hybridization.

"Stringent hybridization conditions" and "stringent hybridization wash conditions" in the context of nucleic acid hybridization experiments such as Southern and Northern blot analysis are both sequence- and environment-dependent. Longer sequences hybridize specifically at higher temperatures. An extensive guide to the hybridization of nucleic acids is found in Tijssen, 1993. Generally, highly stringent hybridization and wash conditions are selected to be about 5° C. lower than the thermal melting point ($T_m$) for the specific sequence at a defined ionic strength and pH. Typically, under "stringent conditions" a probe will hybridize specifically to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for Southern or Northern Blot analysis of complementary nucleic acids having more than about 100 complementary residues is overnight hybridization in 50% formamide with 1 mg of heparin at 42° C. An example of highly stringent wash conditions is 15 minutes in 0.1×SSC at 65° C. An example of stringent wash conditions is 15 minutes in 0.2×SSC buffer at 65° C. See Sambrook & Russell, 2001, for a description of SSC buffer. Often, a high stringency wash is preceded by a low stringency wash to remove background probe signal. An example of medium stringency wash conditions for a duplex of more than about 100 nucleotides is 15 minutes in 1×SSC at 45° C. An example of low stringency wash for a duplex of more than about 100 nucleotides is 15 minutes in 4× to 6×SSC at 40° C. For short probes (e.g., about 10 to 50 nucleotides), stringent conditions typically involve salt concentrations of less than about 1 M $Na^+$ ion, typically about 0.01 to 1M $Na^+$ ion concentration (or other salts) at pH 7.0-8.3, and the temperature is typically at least about 30° C. Stringent conditions can also be achieved with the addition of destabilizing agents such as formamide. In general, a signal to noise ratio of 2-fold (or higher) than that observed for an unrelated probe in the particular hybridization assay indicates detection of a specific hybridization.

The following are examples of hybridization and wash conditions that can be used to identify nucleotide sequences that are substantially identical to reference nucleotide sequences of the presently disclosed subject matter: in one embodiment a probe nucleotide sequence hybridizes to a target nucleotide sequence in 7% sodium dodecyl sulfate (SDS), 0.5 M $NaPO_4$, 1 mM EDTA at 50° C. followed by washing in 2×SSC, 0.1% SDS at 50° C.; in another embodiment, a probe and target sequence hybridize in 7% SDS, 0.5 M $NaPO_4$, 1 mM EDTA at 50° C. followed by washing in 1×SSC, 0.1% SDS at 50° C.; in another embodiment, a probe and target sequence hybridize in 7% SDS, 0.5 M $NaPO_4$, 1 mM EDTA at 50° C. followed by washing in 0.5×SSC, 0.1% SDS at 50° C.; in another embodiment, a probe and target sequence hybridize in 7% SDS, 0.5 M $NaPO_4$, 1 mM EDTA at 50° C. followed by washing in 0.1×SSC, 0.1% SDS at 50° C.; in another embodiment, a probe and target sequence hybridize in 7% SDS, 0.5 M $NaPO_4$, 1 mM EDTA at 50° C. followed by washing in 0.1×SSC, 0.1% SDS at 65° C.

A further indication that two nucleic acid sequences are substantially identical is that proteins encoded by the nucleic acids are substantially identical, share an overall three-dimensional structure, or are biologically functional equivalents. These terms are defined further herein below. Nucleic acid molecules that do not hybridize to each other under stringent conditions are still substantially identical if the corresponding proteins are substantially identical. This can occur, for example, when two nucleotide sequences are significantly degenerate as permitted by the genetic code.

The term "conservatively substituted variants" refers to nucleic acid sequences having degenerate codon substitutions wherein the third position of one or more selected (or all) codons is substituted with mixed-base and/or deoxyinosine residues. See Ohtsuka et al., 1985; Batzer et al., 1991; Rossolini et al., 1994.

The term "subsequence" refers to a sequence of nucleic acids that comprises a part of a longer nucleic acid sequence. An exemplary subsequence is a probe, described herein, or a primer. The term "primer" as used herein refers to a contiguous sequence comprising in one embodiment about 8 or more deoxyribonucleotides or ribonucleotides, in another embodiment 10-20 nucleotides, and in yet another embodiment 20-30 nucleotides of a selected nucleic acid molecule. The primers of the presently disclosed subject matter encompass oligonucleotides of sufficient length and appropriate sequence so as to provide initiation of polymerization on a nucleic acid molecule of the presently disclosed subject matter.

The term "elongated sequence" refers to an addition of nucleotides (or other analogous molecules) incorporated into the nucleic acid. For example, a polymerase (e.g., a DNA polymerase) can add sequences at the 3' terminus of the nucleic acid molecule. In addition, the nucleotide sequence can be combined with other DNA sequences, such as promoters, promoter regions, enhancers, polyadenylation signals, intronic sequences, additional restriction enzyme sites, multiple cloning sites, and other coding segments.

The term "complementary sequences", as used herein, indicates two nucleotide sequences that comprise antiparallel nucleotide sequences capable of pairing with one another upon formation of hydrogen bonds between base pairs. As used herein, the term "complementary sequences" means nucleotide sequences which are substantially complementary, as can be assessed by the same nucleotide comparison set forth above, or is defined as being capable of hybridizing to the nucleic acid segment in question under relatively stringent conditions such as those described herein. A particular example of a complementary nucleic acid segment is an antisense oligonucleotide.

Nucleic acids of the presently disclosed subject matter can be cloned, synthesized, recombinantly altered, mutagenized, or combinations thereof. Standard recombinant DNA and molecular cloning techniques used to isolate nucleic acids are known in the art. Site-specific mutagenesis to create base pair changes, deletions, or small insertions are also known in the art. See e.g., Sambrook & Russell (2001) *Molecular Cloning: a Laboratory Manual*, 3rd ed. Cold Spring Harbor Laboratory Press, Cold Spring Harbor, N.Y.; Silhavy et al. (1984) *Experiments with Gene Fusions*. Cold Spring Harbor Laboratory, Cold Spring Harbor, N.Y.; Glover & Hames (1995) *DNA Cloning: A Practical Approach*, 2nd ed. IRL Press at Oxford University Press, Oxford/New York; Ausubel (1995) *Short Protocols in Molecular Biology*, 3rd ed. Wiley, New York.

TABLE 1

Functionally Equivalent Codons

| Amino Acids | | | Codons |
|---|---|---|---|
| Alanine | Ala | A | GCA GCC GCG GCU |
| Cysteine | Cys | C | UGC UGU |
| Aspartic Acid | Asp | D | GAC GAU |
| Glumatic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | ACG AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

V. Comparison of Nucleotide and Amino Acid Sequences

The terms "identical" or percent "identity" in the context of two or more nucleotide or polypeptide sequences, refer to two or more sequences or subsequences that are the same or have a specified percentage of amino acid residues or nucleotides that are the same, when compared and aligned for maximum correspondence, as measured using one of the sequence comparison algorithms disclosed herein or by visual inspection.

The term "substantially identical" in regards to a nucleotide or polypeptide sequence means that a particular sequence varies from the sequence of a naturally occurring sequence by one or more deletions, substitutions, or additions, the net effect of which is to retain biological activity of a gene, gene product, or sequence of interest. For sequence comparison, typically one sequence acts as a reference sequence to which test sequences are compared. When using a sequence comparison algorithm, test and reference sequences are entered into a computer program, subsequence coordinates are designated if necessary, and sequence algorithm program parameters are selected. The sequence comparison algorithm then calculates the percent sequence identity for the designated test sequence(s) relative to the reference sequence, based on the selected program parameters.

Optimal alignment of sequences for comparison can be conducted, for example by the local homology algorithm of Smith & Waterman, 1981, by the homology alignment algorithm of Needleman & Wunsch, 1970, by the search for similarity method of Pearson & Lipman, 1988, by computerized implementations of these algorithms (GAP, BESTFIT, FASTA, and TFASTA in the Wisconsin Genetics Software Package, available from Accelrys Inc., San Diego, Calif., United States of America), or by visual inspection. See generally, Ausubel, 1995.

An exemplary algorithm for determining percent sequence identity and sequence similarity is the BLAST algorithm, which is described in Altschul et al., 1990. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength W=11, an expectation E=10, a cutoff of 100, M=5, N=-4, and a comparison of both strands. For amino acid sequences, the BLASTP program uses as defaults a wordlength (W) of 3, an expectation (E) of 10, and the BLOSUM62 scoring matrix. See Henikoff & Henikoff, 2000.

In addition to calculating percent sequence identity, the BLAST algorithm also performs a statistical analysis of the similarity between two sequences. See e.g., Karlin & Altschul, 1993. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is in one embodiment less than about 0.1, in another embodiment less than about 0.01, and in still another embodiment less than about 0.001.

VI. Gene Therapy Delivery Systems

The presently disclosed subject matter also provides gene therapy constructs or vectors. The particular vector employed in accordance with the presently disclosed subject matter is not intended to be a limitation of the disclosed and claimed compositions and methods. Thus, any suitable vector, construct or delivery vehicle as would be apparent to those of skill in the art upon a review of the instant disclosure can be used within the scope of the presently disclosed subject matter.

The vector can be a viral vector or a non-viral vector. Suitable viral vectors include adenoviruses, adeno-associated viruses (AAVs), self-complementary AAV (scAAV; Buie et al., 2010 Invest Ophthalmol Vis Sci. 51:236-248), retroviruses, pseudotyped retroviruses, herpes viruses, vaccinia viruses, Semiliki forest virus, and baculoviruses. Suitable non-viral vectors comprise plasmids, water-oil emulsions, polethylene imines, dendrimers, micelles, microcapsules, liposomes, and cationic lipids. Polymeric carriers for gene therapy constructs can be used as described in Goldman et al. (1997) Nat Biotechnol 15:462 and U.S. Pat. Nos. 4,551,482 and 5,714,166. Where appropriate, two or more types of vectors can be used together. For example, a plasmid vector can be used in conjunction with liposomes. Provided in some embodiments of the presently disclosed subject matter is the use of an adenovirus, as described further herein below.

Suitable methods for introduction of a gene therapy construct into cells include direct injection into a cell or cell mass, particle-mediated gene transfer, electroporation, DEAE-Dextran transfection, liposome-mediated transfection, viral infection, and combinations thereof. A delivery method is selected based considerations such as the vector type, the toxicity of the encoded gene, the condition or tissue to be treated and the site of administration and/or treatment.

Viral Gene Therapy Vectors

In some embodiments viral vectors of the presently disclosed subject matter can be disabled, e.g. replication-deficient. That is, they lack one or more functional genes required for their replication, which prevents their uncontrolled replication in vivo and avoids undesirable side effects of viral infection. In some embodiments, all of the viral genome is removed except for the minimum genomic elements required to package the viral genome incorporating the therapeutic gene into the viral coat or capsid. For example, in some embodiments it is desirable to delete all the viral genome except the Long Terminal Repeats (LTRs) or Invented Terminal Repeats (ITRs) and a packaging signal. In the cases of adenoviruses, deletions can be made in the E1 region and optionally in one or more of the E2, E3 and/or E4 regions. In the case of retroviruses, genes required for replication, such as env and/or gag/pol can be deleted. Deletion of sequences can be achieved by recombinant approaches, for example, involving digestion with appropriate restriction enzymes, followed by religation. Replication-competent self-limiting or self-destructing viral vectors can also be used.

Nucleic acid constructs of the presently disclosed subject matter can be incorporated into viral genomes by any suitable approach known in the art. In some embodiments, such incorporation can be performed by ligating the construct into an appropriate restriction site in the genome of the virus. Viral genomes can then be packaged into viral coats or capsids by any suitable procedure. In particular, any suitable packaging cell line can be used to generate viral vectors of the presently disclosed subject matter. These packaging lines complement the replication-deficient viral genomes of the presently disclosed subject matter, as they include, typically incorporated into their genomes, the genes which have been deleted from the replication-deficient genome. Thus, the use of packaging lines allows viral vectors of the presently disclosed subject matter to be generated in culture.

In some embodiments the vector is an adenoviral vector. By way of example and not limitation, adenovirus titration and determination of infectivity are described in the Examples below.

Plasmid Gene Therapy Vectors

In some embodiments, a therapeutic gene can be encoded by a naked plasmid. The toxicity of plasmid DNA is generally low and large-scale production is relatively easy. Plasmid transfection efficiency in vivo encompasses a multitude of parameters, such as the amount of plasmid, time between plasmid injection and electroporation, temperature during electroporation, and electrode geometry and pulse parameters (field strength, pulse length, pulse sequence, etc.). The methods disclosed herein can be optimized for a particular application by methods known to one of skill in the art, and the presently disclosed subject matter encompasses such variations. See, e.g., Heller et al. (1996) FEBS Lett 389:225-228; Vicat et al. (2000) Hum Gene Ther 11:909-916; Miklavcic et al. (1998) Biophys J 74:2152-2158.

Liposomes

The presently disclosed subject matter also provides for the use of gene therapy constructs comprising liposomes. Liposomes can be prepared by any of a variety of techniques that are known in the art. See, e.g., Betageri et al., 1993 Liposome Drug Delivery Systems, Technomic Publishing, Lancaster; Gregoriadis, ed., 1993 Liposome Technology, CRC Press, Boca Raton, Fla.; Janoff, ed. 1999 Liposomes: Rational Design, M. Dekker, New York, N.Y.; Lasic & Martin, 1995 Stealth Liposomes, CRC Press, Boca Raton, Fla.; Nabel, 1997 "Vectors for Gene Therapy" in Current Protocols in Human Genetics on CD-ROM, John Wiley & Sons, New York, N.Y.; and U.S. Pat. Nos. 4,235,871; 4,551,482; 6,197,333; and 6,132,766. Temperature-sensitive liposomes can also be used, for example THERMOSOMES™ as disclosed in U.S. Pat. No. 6,200,598. Entrapment of an active agent within liposomes of the presently disclosed subject matter can also be carried out using any conventional method in the art. In preparing liposome compositions, stabilizers such as antioxidants and other additives can be used.

Other lipid carriers can also be used in accordance with the presently disclosed subject matter, such as lipid microparticles, micelles, lipid suspensions, and lipid emulsions. See, e.g., Labat-Moleur et al., 1996 Gene Therapy 3:1010-1017; U.S. Pat. Nos. 5,011,634; 6,056,938; 6,217,886; 5,948,767; and 6,210,707.

Inducible Gene Therapy Vectors

In some instances a continuous un-regulated overexpression of transgene products could result in an unwanted physiological or toxic effect. Thus, in an effort to maximize expression levels of a gene product encoded by a gene therapy vector at a desired site and/or at a desired time, and concomitantly minimize the constitutive expression and/or systemic levels of the same encoded gene product, constructs of the presently disclosed subject matter can comprise an inducible promoter. As disclosed herein, controlled expression of a therapeutic transgene can be achieved by employing an inducible vector.

In some embodiments, an insult-induced gene therapy construct is provided that increases the levels of its therapeutic product when the agent triggering the disease is present, and stops its mode of action when it is no longer needed. By way of example and not limitation, an inducible gene therapy construct of the presently disclosed subject matter for treating glaucoma can increase expression of its therapeutic peptide, e.g. MMP1, when the construct is in the presence of a steroid, and stop or substantially decrease expression of its therapeutic gene upon the removal or clearance of the steroid.

At least one advantage of an inducible vector is that it is active only when the insult-triggered agent is present. Therefore, rather than a coding sequence for a polypeptide of interest being constitutively expressed, it will be expressed only when needed, that is, when a triggering agent, e.g. a steroid, is present. Thus, by way of example and not limitation, an inducible gene therapy construct of the presently disclosed subject matter expressing RNAi directed to HULLK to downregulate expression of the same.

In some embodiments a gene therapy construct of the presently disclosed subject matter can comprise a steroid response element (SRE). Due to the inducible nature of the SRE, a vector comprising a selected gene and an SRE will express the gene only when exposed to a steroid. In some embodiments, the SRE is a glucocorticoid response element (GRE).

VII. Pharmaceutical Compositions

The presently disclosed subject matter provides pharmaceutical compositions comprising a gene therapy construct or other component of the presently disclosed subject matter. In some embodiments, a pharmaceutical composition can comprise one or more gene therapy constructs or components produced in accordance with the presently disclosed subject matter.

In some embodiments a pharmaceutical composition can also contain a pharmaceutically acceptable carrier or adjuvant for administration of the gene therapy construct. In some embodiments, the carrier is pharmaceutically acceptable for use in humans. In some embodiments, the carrier is pharmaceutically acceptable for use in the eye and associated ocular tissues. The carrier or adjuvant desirably should not itself induce the production of antibodies harmful to the individual receiving the composition and should not be toxic. Suitable carriers can be large, slowly metabolized macromolecules such as proteins, polypeptides, liposomes, polysaccharides, polylactic acids, polyglycolic acids, polymeric amino acids, ammo acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonate and benzoates.

Pharmaceutically acceptable carriers in therapeutic compositions can additionally contain liquids such as water, saline, glycerol and ethanol. Additionally, auxiliary substances, such as wetting or emulsifying agents or pH buffering substances, can be present in such compositions. Such carriers enable the pharmaceutical compositions to be formulated for administration to the patient.

The compositions of the presently disclosed subject matter can further comprise a carrier to facilitate composition preparation and administration. Any suitable delivery vehicle or carrier can be used, including but not limited to a microcapsule, for example a microsphere or a nanosphere (Manome et al. (1994) Cancer Res 54:5408-5413; Saltzman & Fung (1997) Adv Drug Deliv Rev 26:209-230), a glycosaminoglycan (U.S. Pat. No. 6,106,866), a fatty acid (U.S. Pat. No. 5,994,392), a fatty emulsion (U.S. Pat. No. 5,651,991), a lipid or lipid derivative (U.S. Pat. No. 5,786,387), collagen (U.S. Pat. No. 5,922,356), a polysaccharide or derivative thereof (U.S. Pat. No. 5,688,931), a nanosuspension (U.S. Pat. No. 5,858,410), a polymeric micelle or conjugate (Goldman et al. (1997) Cancer Res 57:1447-1451 and U.S. Pat. Nos. 4,551,482, 5,714,166, 5,510,103, 5,490,840, and 5,855,900), and a polysome (U.S. Pat. No. 5,922,545).

Suitable formulations of pharmaceutical compositions of the presently disclosed subject matter include aqueous and non-aqueous sterile injection solutions which can contain anti-oxidants, buffers, bacteriostats, bactericidal antibiotics and solutes which render the formulation isotonic with the bodily fluids of the intended recipient; and aqueous and non-aqueous sterile suspensions which can include suspending agents and thickening agents. The formulations can be presented in unit-dose or multi-dose containers, for example sealed ampoules and vials, and can be stored in a frozen or freeze-dried (lyophilized) condition requiring only the addition of sterile liquid carrier, for example water for injections, immediately prior to use. Some exemplary ingredients are SDS in the range of in some embodiments 0.1 to 10 mg/ml, in some embodiments about 2.0 mg/ml; and/or mannitol or another sugar in the range of in some embodiments 10 to 100 mg/ml, in some embodiments about 30 mg/ml; and/or phosphate-buffered saline (PBS). Any other agents conventional in the art having regard to the type of formulation in question can be used. In some embodiments, the carrier is pharmaceutically acceptable. In some embodiments the carrier is pharmaceutically acceptable for use in humans. In some embodiments the carrier is pharmaceutically acceptable for use in the eye and ocular tissue.

Pharmaceutical compositions of the presently disclosed subject matter can have a pH between 5.5 and 8.5, preferably between 6 and 8, and more preferably about 7. The pH can be maintained by the use of a buffer. The composition can be sterile and/or pyrogen free. The composition can be isotonic with respect to humans. Pharmaceutical compositions of the presently disclosed subject matter can be supplied in hermetically-sealed containers.

VIII. Subjects

The subject treated in the presently disclosed subject matter is desirably a human subject, although it is to be understood that the principles of the disclosed subject matter indicate that the compositions and methods are effective with respect to invertebrate and to all vertebrate species, including mammals, which are intended to be included in the term "subject". Moreover, a mammal is understood to include any mammalian species in which treatment of ocular conditions or treatment or prevention of glaucoma is desirable, particularly agricultural, and domestic mammalian species. The methods of the presently disclosed subject matter are particularly useful in the treatment of warm-blooded vertebrates. Thus, the presently disclosed subject matter concerns mammals and birds.

More particularly, provided herein is the treatment of mammals such as humans, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they are also of economic importance to humans. Thus, provided herein is the treatment of livestock, including, but not limited to, domesticated swine (pigs and hogs), ruminants, horses, poultry, and the like.

In some embodiments, the subject to be treated in accordance with the presently disclosed subject matter is a subject in need of ocular treatment. In some embodiments, a subject in need of ocular comprises a subject suffering from ocular inflammation, macular edema, choroidal neovascularization, or combinations thereof.

IX. Administration

Suitable methods for administration of the compositions, therapeutic formulations and/or gene therapy constructs of the presently disclosed subject matter include but are not limited to intravenous, subcutaneous, or intraocular injection. In some embodiments the gene therapy constructs of the presently disclosed subject matter are administered via sub-Tenon injection or trans-corneal injection. Alternatively, such therapeutic compositions can be deposited at a site in need of treatment in any other manner appropriate for the condition to be treated or the target site. For example, any approach suitable for administration to prostate tissues is within the scope of the presently disclosed subject matter. In some embodiments, the particular mode of administering a therapeutic composition of the presently disclosed subject matter depends on various factors, including the distribution and abundance of cells to be treated, the vector employed, additional tissue- or cell-targeting features of the vector, and mechanisms for metabolism or removal of the vector from its site of administration.

X. Dose

An effective dose of the compositions, therapeutic formulations and/or gene therapy constructs of the presently disclosed subject matter is administered to a subject in need thereof. The terms "therapeutically effective amount", "therapeutically effective dose", "effective amount", "effective dose" and variations thereof are used interchangeably herein and refer to an amount of a therapeutic composition or gene therapy construct of the presently disclosed subject matter sufficient to produce a measurable response (e.g. decreased HULLK expression in a subject being treated).

Actual dosage levels of gene therapy constructs, and in some instances the therapeutic genes expressed by the gene therapy constructs, can be varied so as to administer an amount that is effective to achieve the desired therapeutic response for a particular subject. By way of example and not limitation, in some embodiments the gene therapy constructs can be administered at dose ranging from $5 \times 10^8$ to $1 \times 10^{10}$ virus genomes (vg), which would correspond to $2 \times 10^8$ to $5 \times 10^9$ infectious units (IFU).

In some embodiments, the dosage of the compositions, therapeutic formulations and/or gene therapy constructs of the presently disclosed subject matter can be varied to achieve a desired level of HULLK expression and/or activity in a subject. In some embodiments, a dosage of gene therapy construct of the presently disclosed subject matter can be optimized to treat, prevent or reverse PCa in a subject.

In some embodiments, the quantity of a therapeutic composition of the presently disclosed subject matter administered to a subject will depend on a number of factors including but not limited to the subject's size, weight, age, the target tissue or organ, the route of administration, the condition to be treated, and the severity of the condition to be treated.

In some embodiments the selected dosage level will depend upon the activity of the therapeutic composition, the route of administration, combination with other drugs or treatments, the severity of the condition being treated, and the condition and prior medical history of the subject being treated. However, upon a review of the instant disclosure, it is within the skill of the art to consider these factors in optimizing an appropriate dosage, including for example starting doses of the compound at levels lower than required to achieve the desired therapeutic effect and to gradually increase the dosage until the desired effect is achieved. Moreover, upon review of the instant disclosure one of ordinary skill in the art can tailor the dosages to an individual subject by making appropriate adjustments or variations, as well as evaluation of when and how to make such adjustments or variations, as is routine to those of ordinary skill in the art. The potency of a therapeutic composition can vary, and therefore a "therapeutically effective" amount can vary. However, using the assay methods described herein below, one skilled in the art can readily assess the potency and efficacy of a gene therapy construct of presently disclosed subject matter and adjust the therapeutic regimen accordingly.

EXAMPLES

The following examples are included to further illustrate various embodiments of the presently disclosed subject matter. However, those of ordinary skill in the art should, in light of the present disclosure, appreciate that many changes can be made in the specific embodiments which are disclosed and still obtain a like or similar result without departing from the spirit and scope of the presently disclosed subject matter.

Materials and Methods for Examples 1-7

Cell Culture and Reagents. LNCaP and C4-2 cells (a gift from Dr. L. W. K. Chung) were grown in DMEM:F12 (Invitrogen) with 5% Non-Heat-Inactivated serum (Gemini) and 1% Insulin-Transferrin-Selenium-Ethanolamine (ThermoFisher). CWR22Rv1 (Rv1), VCaP, PC3 (gifts from Drs. Steven Balk, Karen Knudsen, and Chung, respectively), WMPY-1 (ATCC), MCF7, BT549 and MDA-MB-231 (gifts from Dr. Amy Bouton) were grown in DMEM (Invitrogen) with 10% Heat-Inactivated serum. DU145 (a gift from Dr. Chung), PANC1 (a gift from Dr. J. Thomas Parsons), HeLa and Jurkat cells (gifts from Dr. Tim Bender) were grown in RPMI-1640 (Invitrogen) with 10% Heat-Inactivated serum. LHS cells (a gift from Dr. William Hahn) were grown in ProstaLife Epithelial Cell Medium (Lifeline). RWPE-1 (ATCC) cells were grown in Keratinocyte-Serum-Free Media (Invitrogen). For growth and RNA experiments, phenol-red free DMEM:F12 media with 5% Charcoal-Stripped Serum (CSS) (Gemini) was used.

Antibodies: ERK1/2 (137F5), Histone H3, LCK (73A5) (c-term), p53 (DO-7), Ran, α-Tubulin (Cell Signaling); LCK (n-term) (BD Biosciences); AR (in-house to first 21aa). Western blotting performed as previously described (17,18).

HULLK primers were based on the human LCK sequence obtained from Genbank (BC013200.1) (FIG. 1A). PCR was performed using iProof High-Fidelity DNA Polymerase (Bio-Rad) and LNCaP cDNA as the template. HULLK was ligated into the lentiviral expression vector PLX301 (a gift from David Root, Addgene plasmid #25895) using Gateway Cloning (ThermoFisher), transformed into DH5a competent bacteria (Life Technologies), and clones were sequenced for verification.

CyQuant Growth Assays: Assay was performed as previously described (18). Briefly, shRNA or pLKO control virus was added to 1 μg/ml fibronectin-coated 96 well plates. Cells were plated in RPMI-1640 plus 5% CSS with vehicle, 0-0.05 nM R1881, and/or 10 μM Enzalutamide (Selleck Chemicals). Quantification was performed on Day 7 using a BioTek Synergy 2 plate reader.

Rapid Amplification of cDNA Ends (RACE): 5' and 3' RACE was performed according to the manufacturer's protocol (Invitrogen) using an anti-sense primer specific for LCK exon 11 (5' RACE) and a sense primer for LCK exon 9 (3' RACE). 5'/3' RACE PCR products were ligated into the pGEM sequencing vector, and multiple clones were sequenced and aligned using the UCSC genome browser.

RNA Isolation, qPCR and ddPCR: RNA was collected using TRIzol and quantitated using a NanoDrop 2000 UV-Vis Spectrophotometer (ThermoFisher). cDNA was synthesized using Superscript IV VILO cDNA synthesis kit (Invitrogen). Quantitative real-time PCR (qPCR) was performed as previously described (17,18). Droplet digital PCR (ddPCR) was executed according to the manufacturer's protocol (Bio-Rad).

Patient Samples: Formalin-fixed paraffin-embedded (FFPE) tissue was minced and deparaffinized prior to RNA isolation. Fresh-frozen tissue was homogenized with a mortar and pestle prior to RNA collection.

TCGA prostate cancer cohort: The LCK exon-specific RSEM data for all samples in TCGA-PRAD cohort (32) was obtained from TSVdb (33) and the sum of RSEM values in exons 9-12 was compared to exons 1-3 to determine a 3'/5' ratio and define HULLK expression as an increase in the 3'/5' ratio. Clinical data for the TCGA-PRAD cohort was down loaded from cBioPortal and LCK 3'/5' ratio was examined comparing normal to tumor and, in tumors only, low Gleason [scores 6 and 7(3+4)] to high Gleason score [scores 7(4+3), and 8-10].

Example 1

Discovery of a Novel lncRNA in PCa Cells

A kinome screen was performed in LNCaP cells grown in the presence or absence of androgen with a panel of shRNAs that targeted the kinome in order to discover potential regulators of growth. The screen identified LCK as a potential positive regulator of growth. Since LCK expression is established in the bone marrow and immune system, but not prostate, initially testing was done for LCK expression in the hormone-sensitive LNCaP and castration-resistant C4-2 cells by western blotting. LCK protein expression was non-detectable in LNCaP and C4-2 cells with standard western blots (FIG. 1A). To improve sensitivity to detect LCK protein, immunoprecipitation using an antibody that recognized the carboxy-terminal of the protein ($LCK^{c-term}$) was performed (FIG. 1A). As expected, immunoblots showed that two independent LCK antibodies, $LCK^{c-term}$ and an amino-terminal LCK antibody ($LCK^{n-term}$), detected the 56 kDa protein in the Jurkat control cells, which express full-length LCK (FL-LCK). Surprisingly, LCK protein was not detected in LNCaP or C4-2 cells under FBS, CSS, or 1 nM R1881 conditions, suggesting that LCK protein may not be expressed in these cells.

Figure 1B:
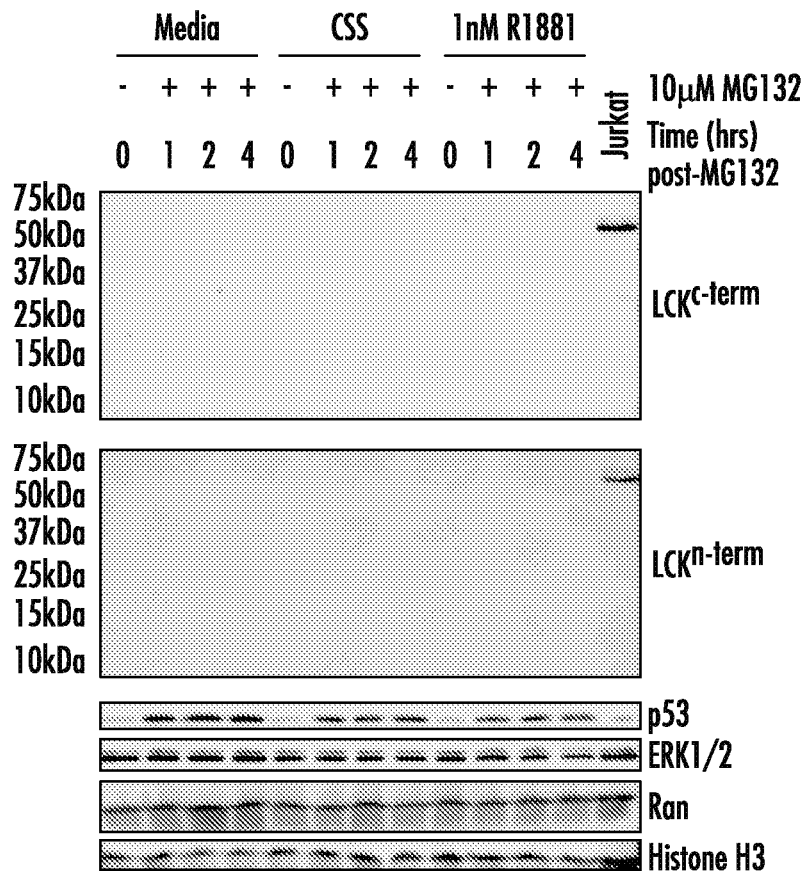
Figure 1C:
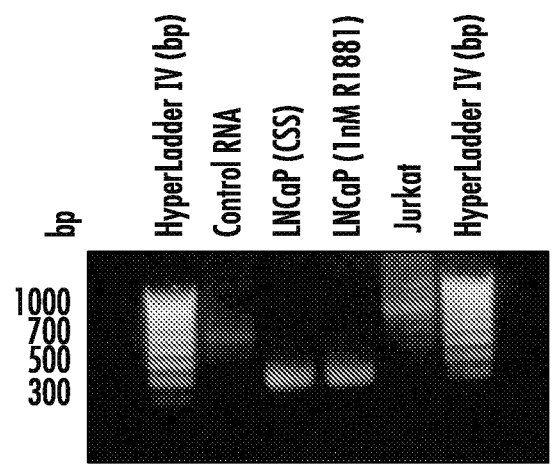
Figure 1C:
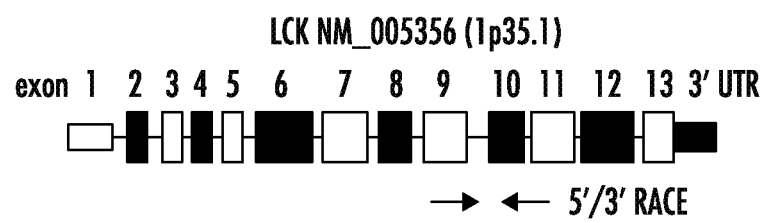
Figure 1D:
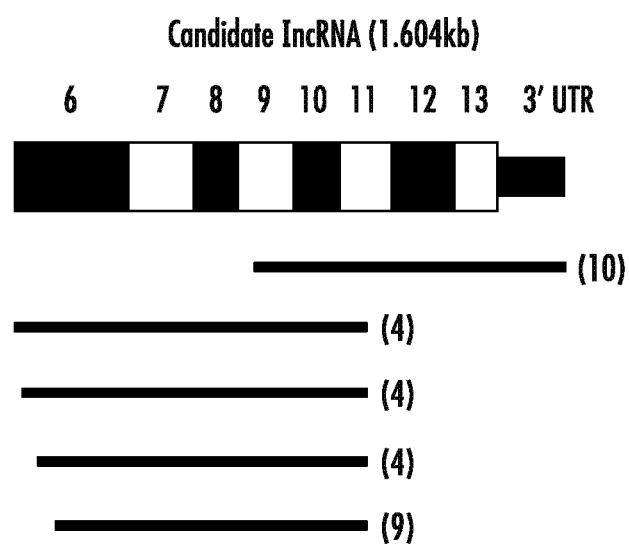

While it has been reported that LCK protein in T-cells has an approximate 20-30 hr half-life (19), several Src family members are downregulated following activation as a result of ubiquitination and degradation by the proteasome (20-22). To determine whether the lack of LCK expression was due to proteasomal degradation, LCK protein levels were examined in the presence of the proteasome inhibitor MG132 (FIG. 1B). The proteasome was successfully blocked since p53, a short-lived protein with a 5-20 min half-life, is elevated in MG132-treated cells (23). As expected, both $LCK^{c-term}$ and $LCK^{n-term}$ antibodies recognized FL-LCK in Jurkat cells. However, LCK was still not observed at any timepoint examined in LNCaP cells treated with FBS, CSS, or 1 nM R1881. Furthermore, no truncated forms of LCK were detected when the whole western blot membrane was probed from 75 kD to 10 kD with either c- or n-terminal LCK antibodies. Thus, these data suggest that LCK protein is not expressed in PCa cells. Therefore, a ncRNA may play a role in the growth effects measured in the kinome screen.

ncRNAs represent over 70% of the human genome and are broadly divided into two main categories: short (<200 bases) and long (>200 bases) noncoding transcripts (16). To determine the full-length sequence of the disclosed ncRNA, 5' and 3' RACE was performed (FIG. 1C). Numerous clones (n=31) were selected, purified, and sequenced. The sequence alignment of these clones from the 5'/3' RACE showed that the ncRNA transcript completely overlapped exon 6 through the 3' untranslated region (3'UTR) of the LCK gene (FIG. 1D). Thus, these data show the identification of a novel lncRNA situated within the LCK gene locus that measures 1604 bases in length.

Example 2

HULLK is an AR-Regulated lncRNA

Figure 2A:
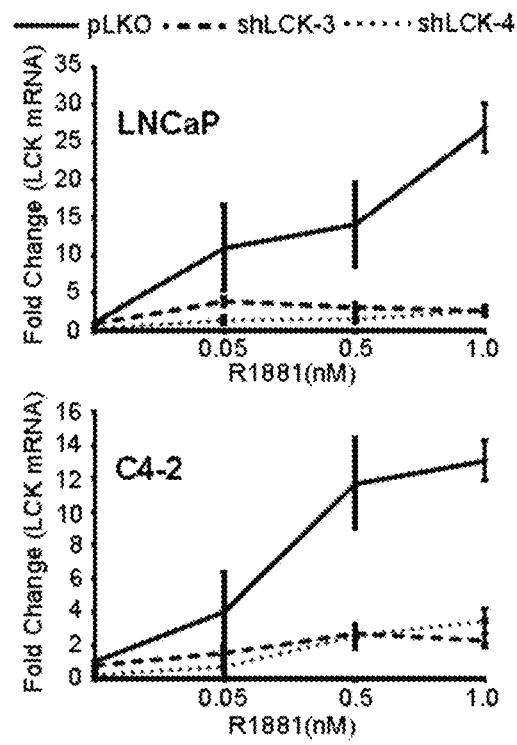
FIGS. 2A through 2E illustrate that HULLK is an AR-regulated lncRNA.

To assess whether this lncRNA is modulated by hormone, transcript levels of this lncRNA were quantified by qPCR using 3'UTR primers in LNCaP and C4-2 cells transduced in the presence of increasing concentrations of R1881 (FIG. 2A). A dose-dependent increase in lncRNA transcripts was found in response to R1881. This increase was inhibited in the presence of two independent LCK shRNAs in both cell lines. This data suggests that the expression of this lncRNA is regulated by androgen.

Figure 2B:
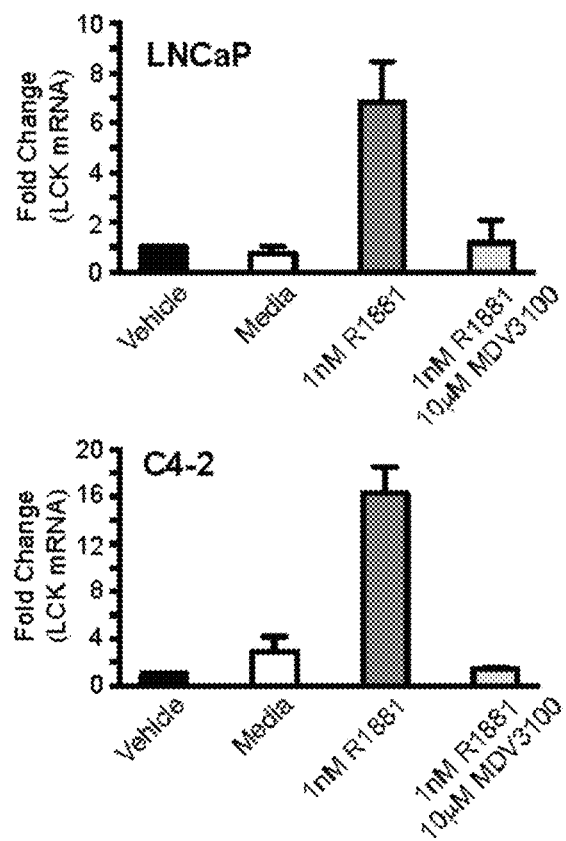
Figure 2C:
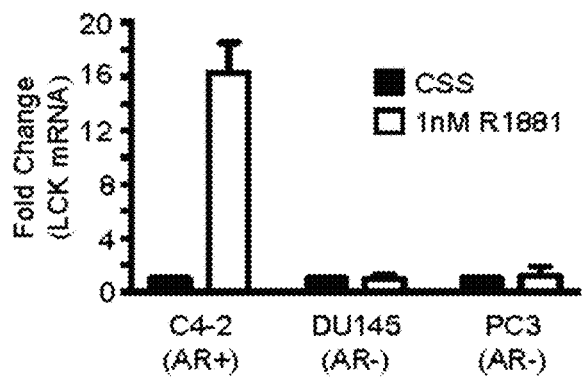

This hormone regulation was confirmed by measuring transcript amounts in LNCaP and C4-2 cells treated with vehicle or R1881 in the presence or absence of the antiandrogen enzalutamide (FIG. 2B). As expected, there was an 8-fold and 12-fold R1881-induced increase in LCK 3'UTR transcript levels in LNCaP and C4-2 cells, respectively. Enzalutamide blocked the hormone-mediated increase in both cell lines. Androgen deprivation influenced message levels negligibly in LNCaP cells, but decreased transcript amounts of this lncRNA by approximately 2.9-fold in C4-2 cells (FIG. 2B, C4-2 vehicle vs. media). There was no R1881-induced increase in this lncRNA in AR-null DU145 and PC3 cells, validating that the AR regulates the expression of this lncRNA (FIG. 2C). As a result of this regulation, it was decided to name this lncRNA HULLK, short for Hormone Upregulated lncRNA within LCK.

Figure 2D:
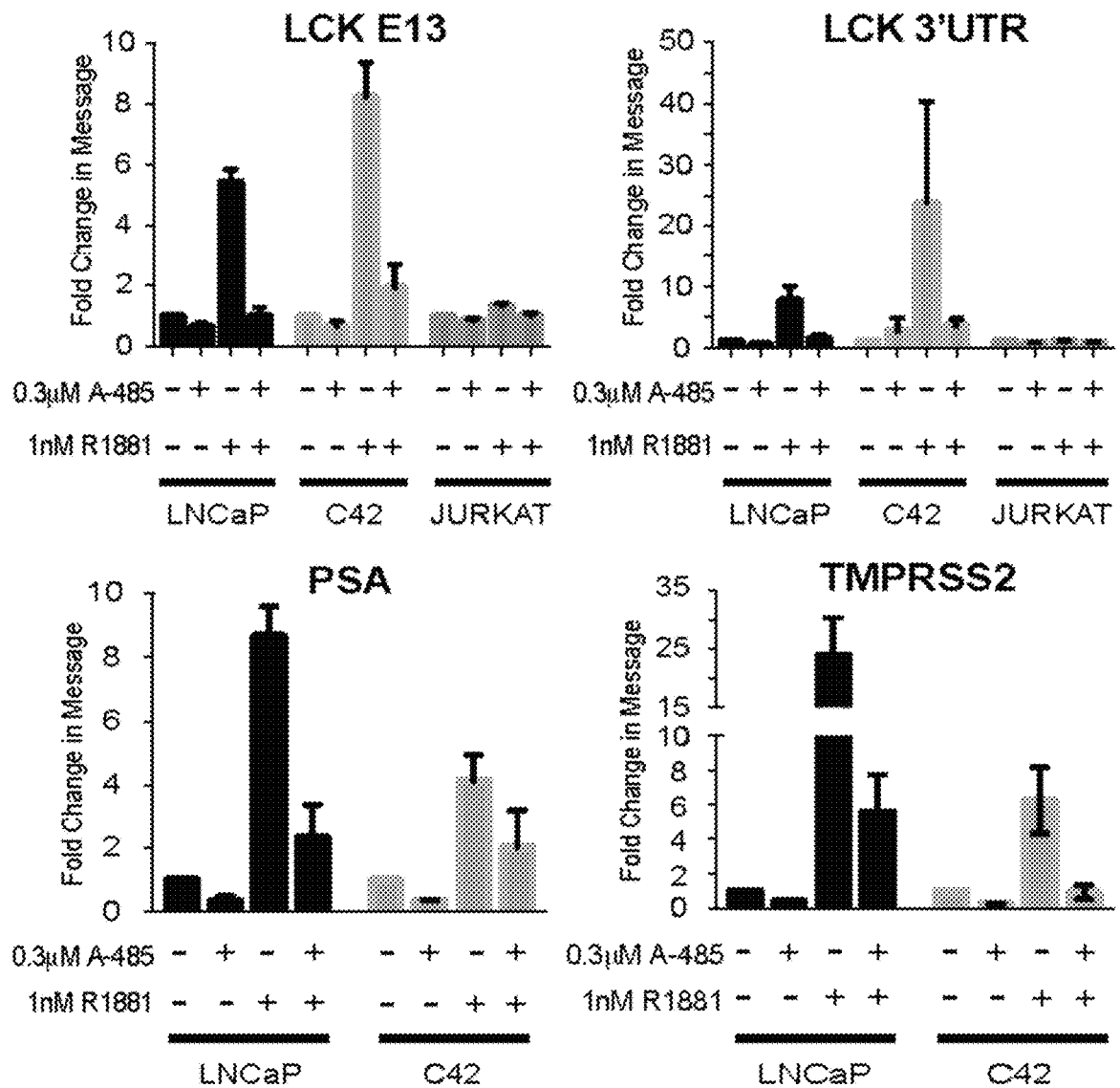
Figure 2E:
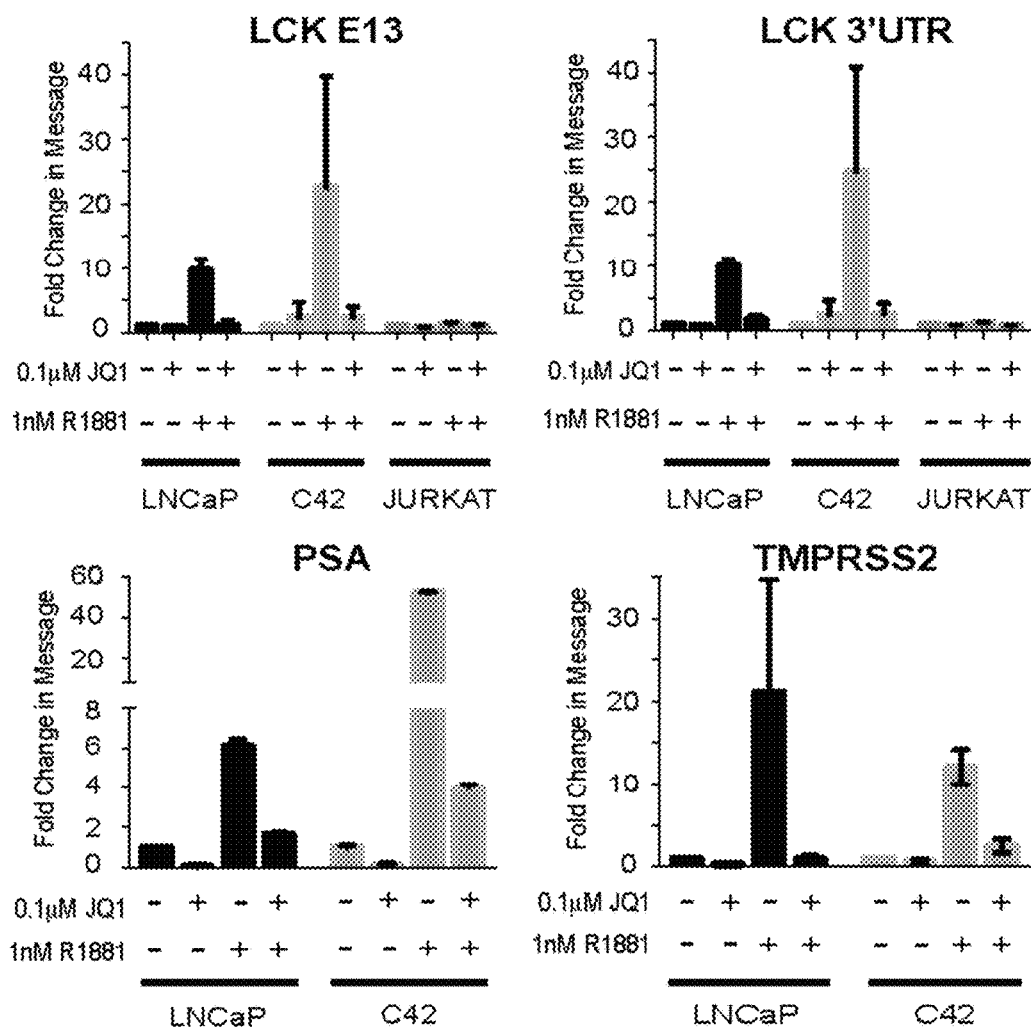

AR coregulators have been shown to be influential in the progression of prostate cancer to castration resistance (24). As disclosed herein, binding sites for two AR coactivators (p300 and Brd4) near the HULLK TSS were discovered. p300 is known to transactivate the AR in an androgen-dependent (25) and androgen-independent manner (26). To assess whether p300 is involved in the regulation of HULLK expression by AR, LNCaP, C4-2, and Jurkat cells were treated with the p300 inhibitor A-485 in the presence and absence of 1 nM R1881 and measured HULLK expression by qPCR using two independent LCK primer pairs (FIG. 2D). The results showed that A-485 alone had negligible effects on HULLK expression. However, the p300 inhibitor significantly opposed the hormone-induced increase in HULLK transcript levels. Analysis of PSA and TMPRSS2 message in the presence of hormone and p300 inhibitor suggests that A-485 was sufficiently blocking its target. Similar effects were observed on HULLK expression when Brd4 was suppressed with the BET family small molecule inhibitor JQ1 (FIG. 2E). Brd4 physically associates with the amino-terminal domain of AR, and recruits RNA polymerase II to promote the transcription of target genes (27). HULLK expression was significantly decreased in the presence of hormone and JQ1, compared to hormone alone. Therefore, these data together indicate that the AR may regulate HULLK expression through the recruitment of p300 and Brd4.

Figure 6A:
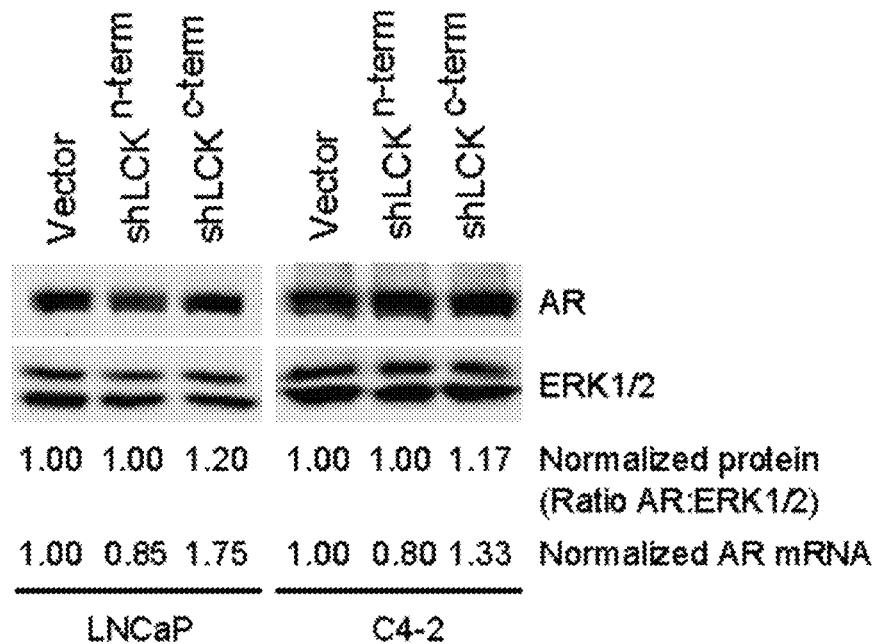
FIGS. 6A and 6B illustrate that HULLK expression does not affect AR expression.
Figure 6B:
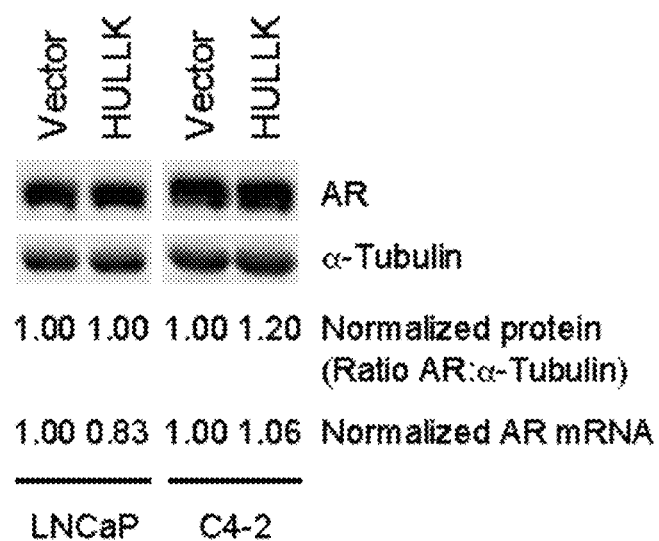

Conversely, studies were conducted to determine whether HULLK modulates AR expression. LNCaP and C4-2 cells were transduced with vector, HULLK, or shRNAs targeting LCK (n-term) (FL-LCK) or LCK (c-term) (HULLK), and AR protein and message levels were examined 48 hrs after transduction. Knockdown of HULLK did not significantly affect levels of AR protein or mRNA (FIG. 6A). Furthermore, AR expression was not notably altered by the overexpression of HULLK (FIG. 6B). Therefore, these data suggest that HULLK is an AR-regulated lncRNA that does not reciprocally influence expression of AR itself.

Example 3

Characterization of HULLK

Figure 3A:
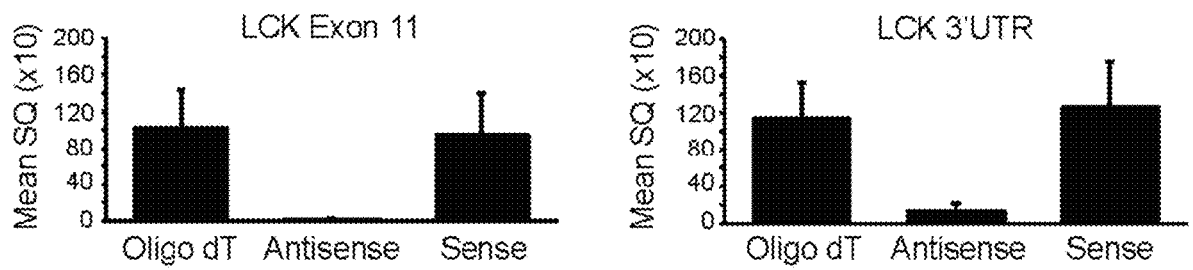
FIGS. 3A and 3B illustrate the results of studies designed to characterize HULLK.

Since lncRNAs can be derived from many different genomic locations and transcribed from either DNA strand, strand-specific qPCR was used to determine which DNA strand HULLK is transcribed from. Total RNA was collected from LNCaP cells grown in complete media, and cDNA template was synthesized using Oligo(dT)16, antisense strand-specific, or sense strand-specific primers. See Table 2 for PCR primer sequences, including HULLK cloning primers, 5'/3' RACE primers, strand-specific PCR primers, and lncRNA localization primers. qPCR was performed with LCK Exon 11 and LCK 3'UTR primer pairs (Table 2). Amplification of PCR products from both LCK primer pairs was only observed with the Oligo(dT)16 and sense strand-specific cDNA templates (FIG. 3A). However, there was no significant PCR amplification from either LCK primer pair when antisense strand-specific cDNA was used as the template. These data indicate that HULLK is transcribed from the sense strand of DNA.

TABLE 2

| PCR Primer Sequences | | |
|---|---|---|
| | Sequence | SEQ ID NO |
| HULLK Cloning Primers | | |
| HULLK-attB1-Forward | 5'-GGGGACAAGTTTGT ACAAAAAAGCAGGCTTC CTGGTTCTTCAAGAACC TGAG-3' | 2 |
| HULLK-attB1-Start-Forward | 5'-GGGGACAAGTTTGTA CAAAAAAGCAGGCTTCGA AGGAGATAGAACCATGGC TGGTTCTTCAAGAACCT GAG-3' | 3 |
| HULLK-attB2-Reverse | 5'-GGGGACCACTTTGTA CAAGAAAGCTGGGTCTCA TCAACAGACATTTATTGA ACTC-3' | 4 |
| HULLK-attB2-Stop-Reverse | 5'-GGGGACCACTTTGTA CAAGAAAGCTGGGTCCTA TCATCAACAGACATTTAT TGAACTC-3' | 5 |
| 5' RACE Primers | | |
| LCK-GSP1-Reverse | 5'-CTTCGTGTGCCCGTT GTAGTA-3' | 6 |
| LCK-GSP2-Reverse | 5'-CCCGAAGGTCACGAT GAATAT-3' | 7 |
| 3' RACE Primers | | |
| LCK-GSP1-Forward | 5'-TACCAACTCATG AGGCTGTGC-3' | 8 |
| LCK Sense-Strand Primer | 5'-CAGACATTTATTGA ACTCCTGA-3' | 9 |
| LCK Anti-Sense-Strand Primer | 5'-ATCGTTTTCACTG TCGGT-3' | 10 |
| LCK Primers: | | |
| LCK Exon 2 | (F)5-GTGTGAGAACTG CCATTATC-3' | 11 |
| | (R)5'-AGAGCCATTTC GGATGAG-3' | 12 |
| LCK Exon 4 | (F)5-CAACCTGGTTAT CGCTCT-3' | 13 |
| | (R)5'-CCTTCTCAAAG CCCAGAT-3' | 14 |
| LCK Exon 11 | (F)5-ATGGCATTCATT GAAGAGC-3' | 15 |
| | (R)5-GTCAGACACCAG AATGTTG-3' | 16 |
| LCK Exon 13 | (F)5-GGAGCTGTACCA ACTCAT-3' | 17 |

TABLE 2-continued

PCR Primer Sequences

| | | |
|---|---|---|
| | (R)5-CAGGTAGTCAAAGGTGGG-3' | 18 |
| LCK 3'UTR | (F)5-ATCCAGAAGTTCCTCAAG-3' | 19 |
| | (R)5'-TTACAACAGTCATCAACAG-3' | 20 |
| lncRNA Primers: | | |
| DANCR | (F)5'-CGGAGGTGGATTCTGTTA-3' | 21 |
| | (R)5-GTGTAGCAAGTCTGGTGA-3' | 22 |
| NEAT | (F)5-GGTCTGAGGAGTGATGTG-3' | 23 |
| | (R)5'-AAGCGTTGGTCAATGTTG-3' | 24 |

Figure 3B:
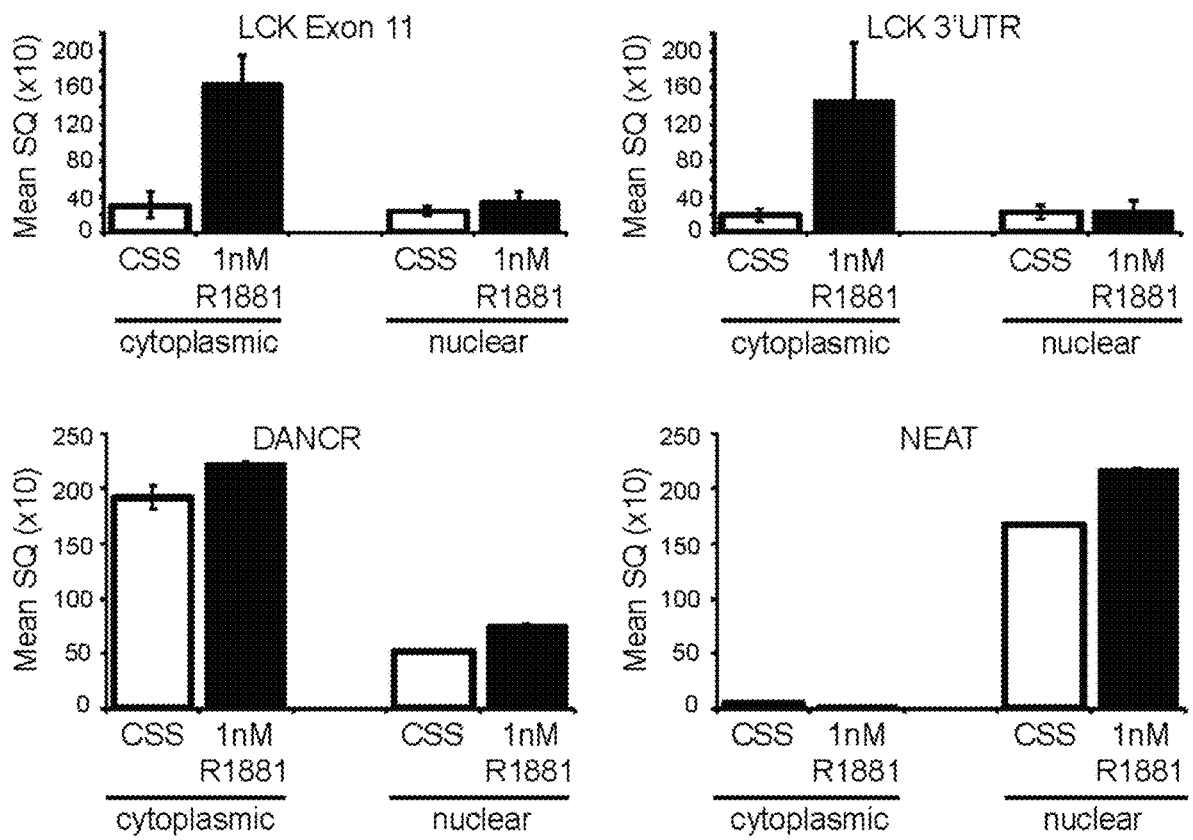

Some lncRNAs show preferential accumulation in the cytoplasm or nucleus, while other lncRNAs are equally expressed in both compartments. To determine the intracellular localization of HULLK, total RNA was collected to synthesize cDNA from cytoplasmic and nuclear fractions of LNCaP cells starved of hormone or exposed to 1 nM R1881 for 24 hrs and carried out qPCR with LCK E11 and LCK 3'UTR primers to amplify HULLK. Amplification of a predominantly cytoplasmic lncRNA DANCR (28) and nuclear lncRNA NEAT1 (29) showed that transcript levels under both conditions were substantially higher in the cytoplasm for DANCR and nucleus for NEAT1, indicating efficient cellular fractionation (FIG. 3B). It was observed that hormone dramatically increased LCK E11 and LCK 3'UTR transcript levels approximately 5.3-fold and 7.6-fold, respectively, in the cytoplasmic fraction, whereas the nuclear transcript amounts were approximately equivalent to the cytoplasmic CSS condition and not influenced by androgens. These results indicate that HULLK is localized to the cytoplasm.

Example 4

HULLK Expression in PCa

Figure 4A:
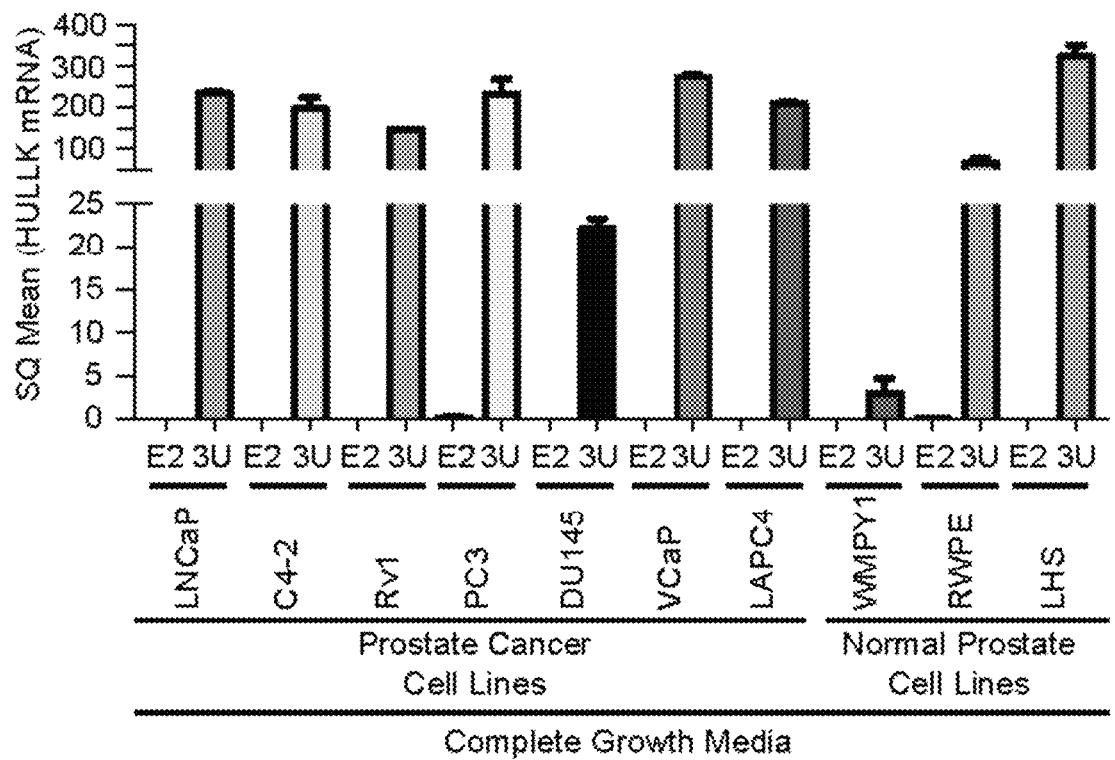

Since HULLK was previously unannotated, little is known about its expression pattern. As the data herein shows, HULLK was discovered in PCa cells, and thus, a panel of PCa and normal prostate epithelial cell lines cultured in their corresponding growth media were surveyed for HULLK expression by qPCR (FIG. 4A). Since the sequence of HULLK overlapped LCK exon 6 through the 3'UTR, the fact that HULLK lacked exons 1-5 was exploited to distinguish HULLK expression from FL-LCK. Therefore, two LCK primer pairs—LCK 3'UTR and LCK exon 2 (LCK E2) were utilized. LCK 3'UTR primers should amplify HULLK as well as FL-LCK; however, LCK E2 primers should only detect FL-LCK. Analysis of seven PCa cell lines (LNCaP, C4-2, CWR22Rv1, PC3, DU145, VCaP, LAPC4) and three normal prostate cell lines (WMPY1, RWPE, LHS) revealed that HULLK is expressed to varying degrees in all cell lines examined, as PCR amplification was only detected with the LCK 3'UTR primers and not the LCK E2. As a control for primer efficiency, FL-LCK was detected in Jurkat cells with both primer pairs (data not shown). These data show that HULLK can be successfully detected by employing this qPCR method of two primer pairs targeting two specific regions in LCK—exons 1-5 and exon 6-3'UTR.

Figure 4B:
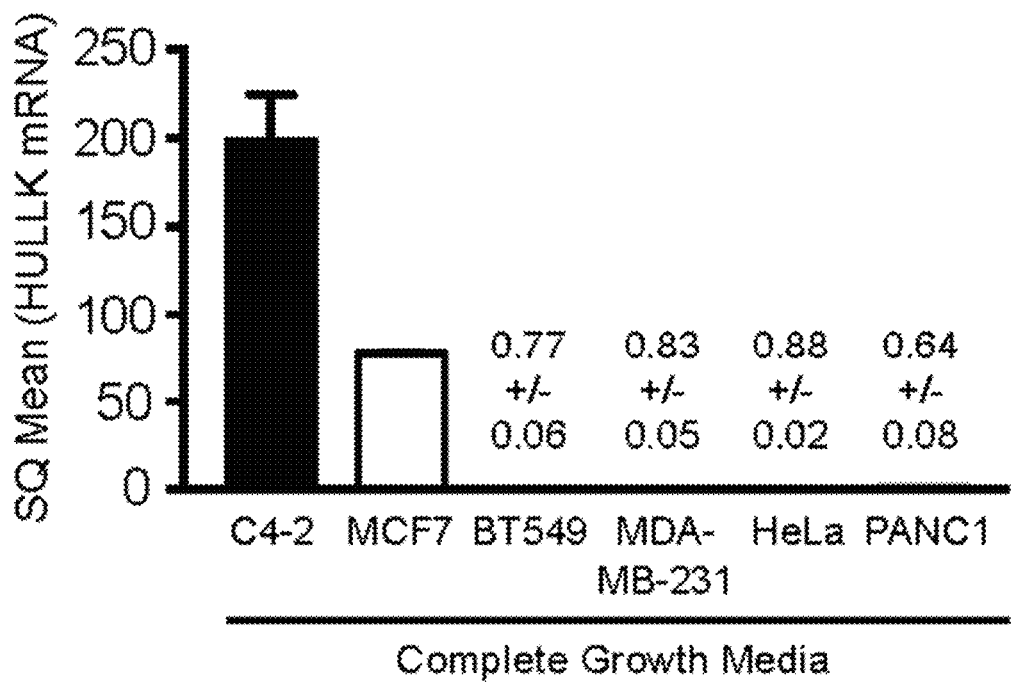

HULLK expression was also examined in other cancer tissue types and no transcripts were observed in cervical (HeLa) or pancreatic (PANC1) cancer cell lines grown under normal serum conditions (FIG. 4B). HULLK was detected in the ER+AR+ luminal A subtype MCF7 breast cancer (BCa) cell line but not in the triple negative Claudin-low BT549 or MDA-MB-231 BCa cell lines (31).

Figure 4C:
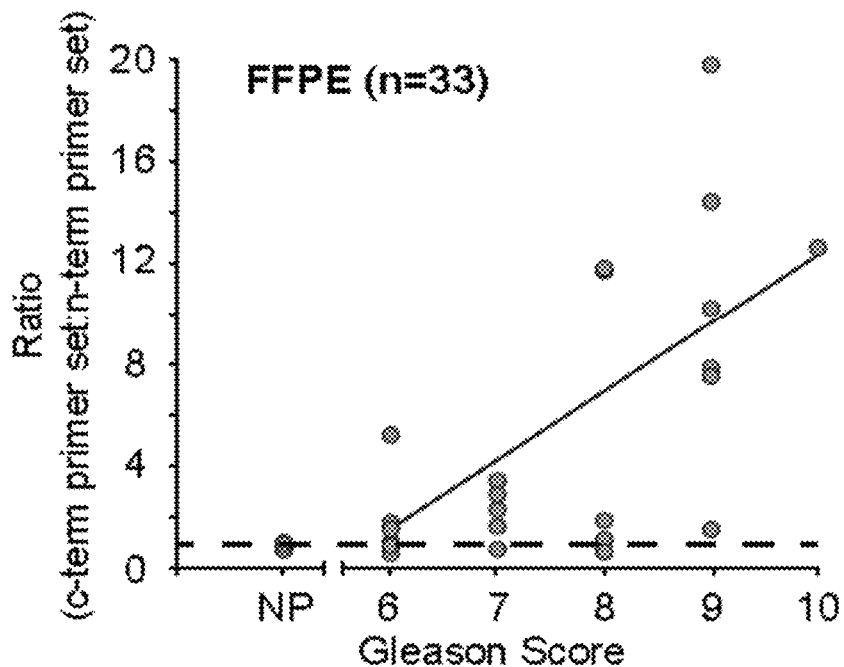
Figure 4D:
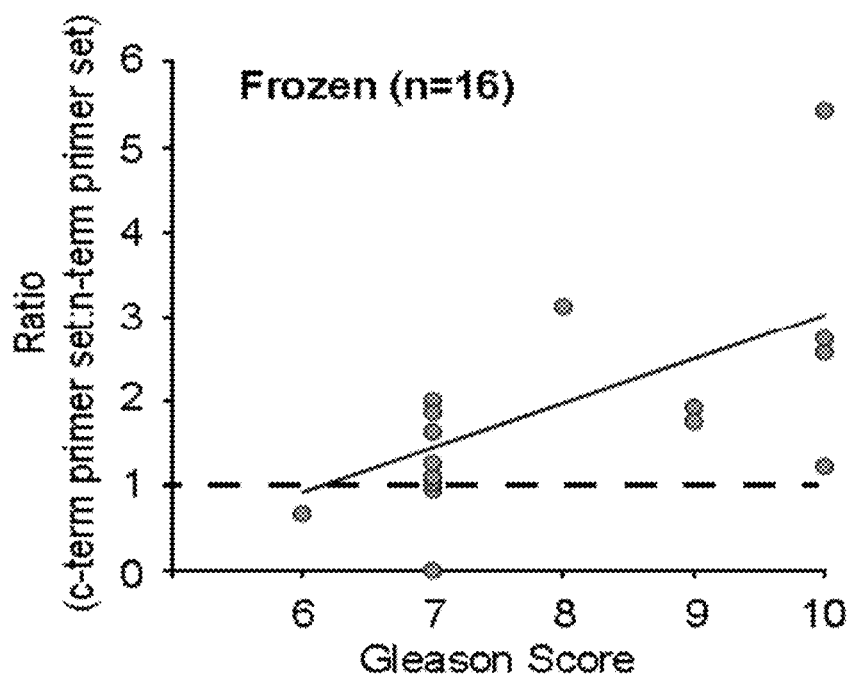

Applying the two LCK primer pair method, HULLK levels were determined in twenty-six FFPE PCa tissue samples from patients presenting with Gleason score 6-10 disease and seven normal prostate tissue obtained from the University of Virginia Biorepository and Tissue Research Facility (FIG. 4C). The results were displayed as the ratio of SQ mean of the carboxy-terminal primer pairs to the amino-terminal primer pair, where <1 indicates FL-LCK and >1 indicates more HULLK. HULLK expression was not detected in the normal prostate tissue that were examined. However, a significant positive correlation was found between HULLK expression and higher Gleason score. This correlation was confirmed using a second cohort of sixteen fresh-frozen PCa tissue from the University of Texas Southwestern (FIG. 4D). In this cohort, similar results were discovered as the first cohort; there was a significant increase in HULLK expression with increased Gleason score. Statistical analyses revealed that pooling the data from the two cohorts does not diminish the significance of this correlation between HULLK levels and Gleason score (FIG. 4E). Finally, the PRAD TCGA cohort (32) was interrogated for HULLK expression and association with clinical correlate. The LCK exon-specific RSEM data for all samples in this cohort was obtained from TSVdb (33), to calculate the 3'/5' ratio and define HULLK expression as an increase in the 3'/5' ratio. An increase in HULLK expression was found when comparing normal to tumor and, in tumors only, low Gleason [scores 6 and 7(3+4)] to high Gleason score [scores 7(4+3), and 8-10]. Interestingly, very high 3'/5' ratios were found in the PRAD TCGA dataset. However, applying a multivariate Cox Proportional Hazards model, controlling for age and Gleason grade, the data did not reveal whether HULLK expression alone was significantly associated with shorter time to biochemical recurrence (data not shown). These data strongly indicate that HULLK is expressed in PCa patients and upregulated with advanced disease.

Example 5

HULLK Positively Regulates PCa Cell Growth

Figure 5A:
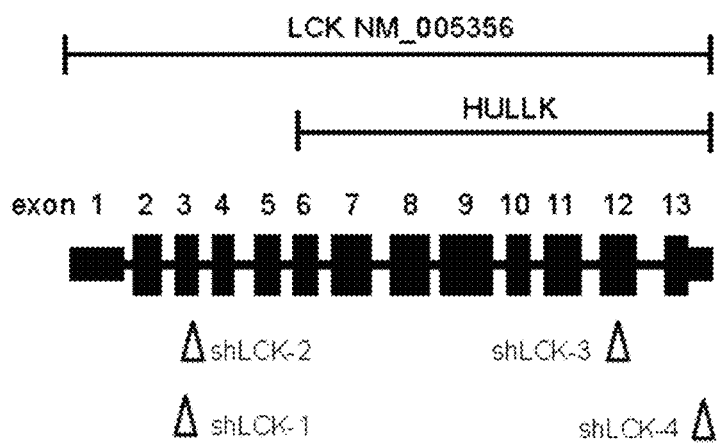
FIGS. 5A through 5D demonstrate that HULLK positively regulates prostate cancer cell growth.
Figure 5B:
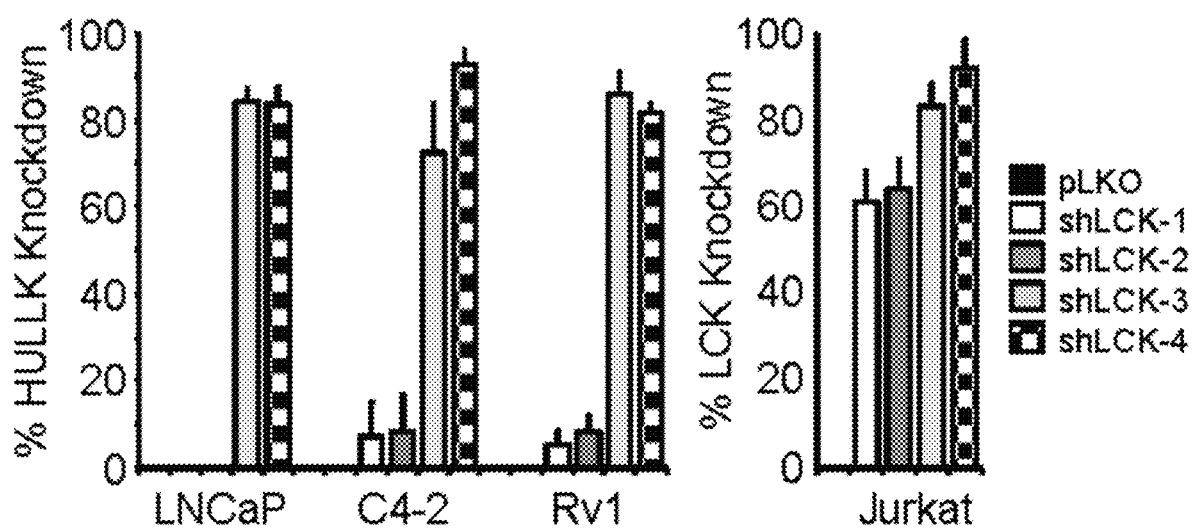
Figure 5C:
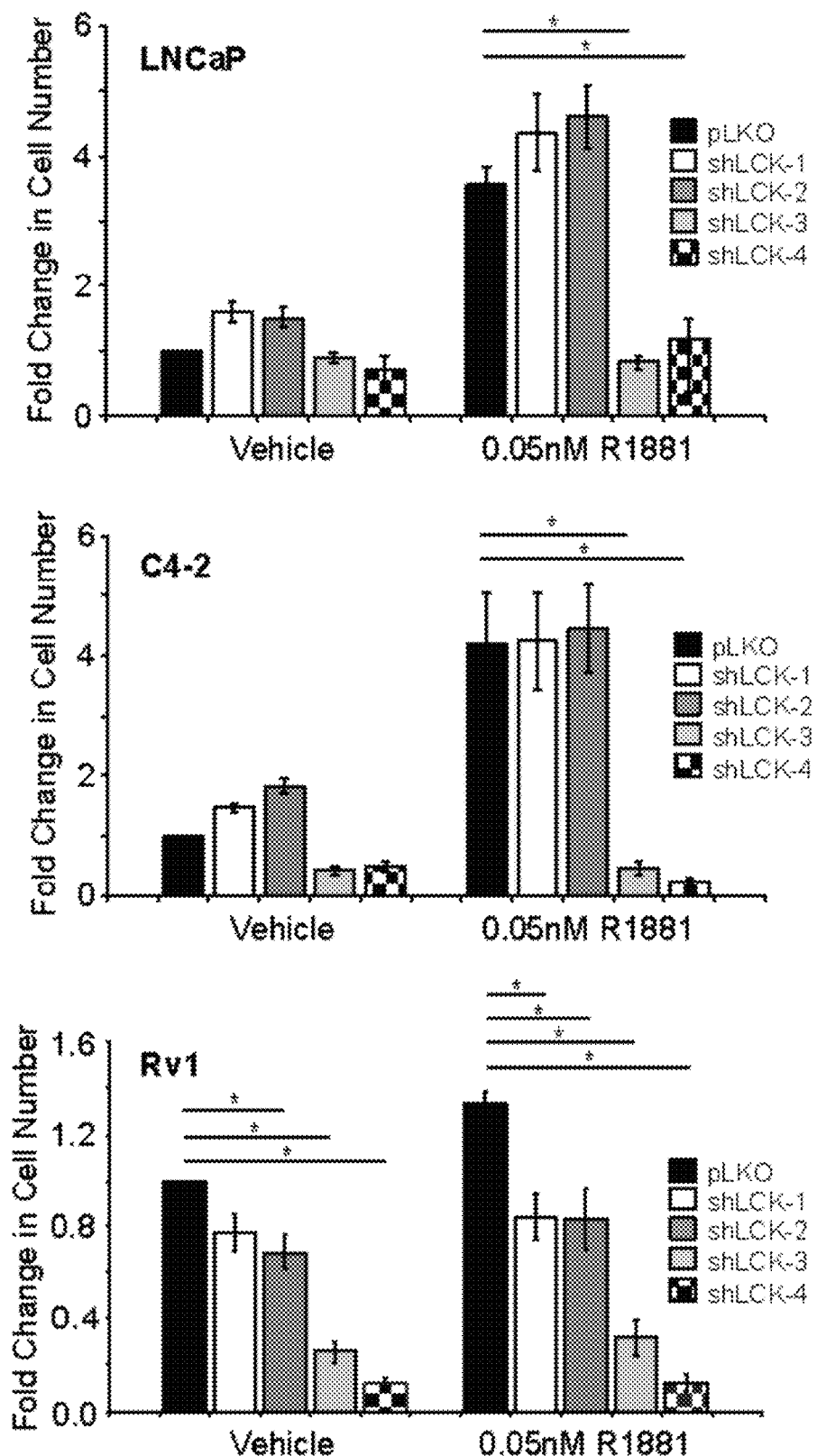

To explore the functional role of HULLK in PCa, the effects of HULLK knockdown on PCa cell growth was examined. LNCaP, C4-2, and Rv1 cells were transduced with lentiviral particles expressing four independent shRNAs specific for LCK or pLKO empty vector control in the presence or absence of 0.05 nM R1881. Two shRNAs were targeting the carboxy-terminal of LCK (shLCK-3 and shLCK-4) and should decrease HULLK levels; and two shRNAs were directed toward the amino-terminal (shLCK-1 and shLCK-2) and should not affect HULLK expression (FIG. 5A). It was confirmed by qPCR that shLCK-3 and shLCK-4 decreased HULLK expression by 70-90% in LNCaP, C4-2, and Rv1 cells (FIG. 5B). shLCK-1 and shLCK-2 had little to no effect on HULLK expression in these three cell lines. As a control, all four shRNAs efficiently knocked LCK down 60-90% in Jurkat cells. Seven days following viral transduction, cellular growth was measured using CyQuant, which uses DNA content as a surrogate for cell number. In the absence of hormone, the four shRNAs had no dramatic effects on growth in LNCaP or C4-2 cells (FIG. 5C). However, there was a statistically significant decrease in cell growth in Rv1 cells with shLCK-2, shLCK-3, and shLCK-4. In the presence of 0.05 nM R1881, the carboxy-terminal shRNAs significantly inhibited growth of LNCaP, C4-2, and Rv1 cells compared to the pLKO control cells. While the amino-terminal shRNAs did not have any significant effects on growth in LNCaP or C4-2 cells, there was a notable proliferative decrease in Rv1 cells. These data suggest that HULLK may drive PCa cell growth.

Figure 5D:
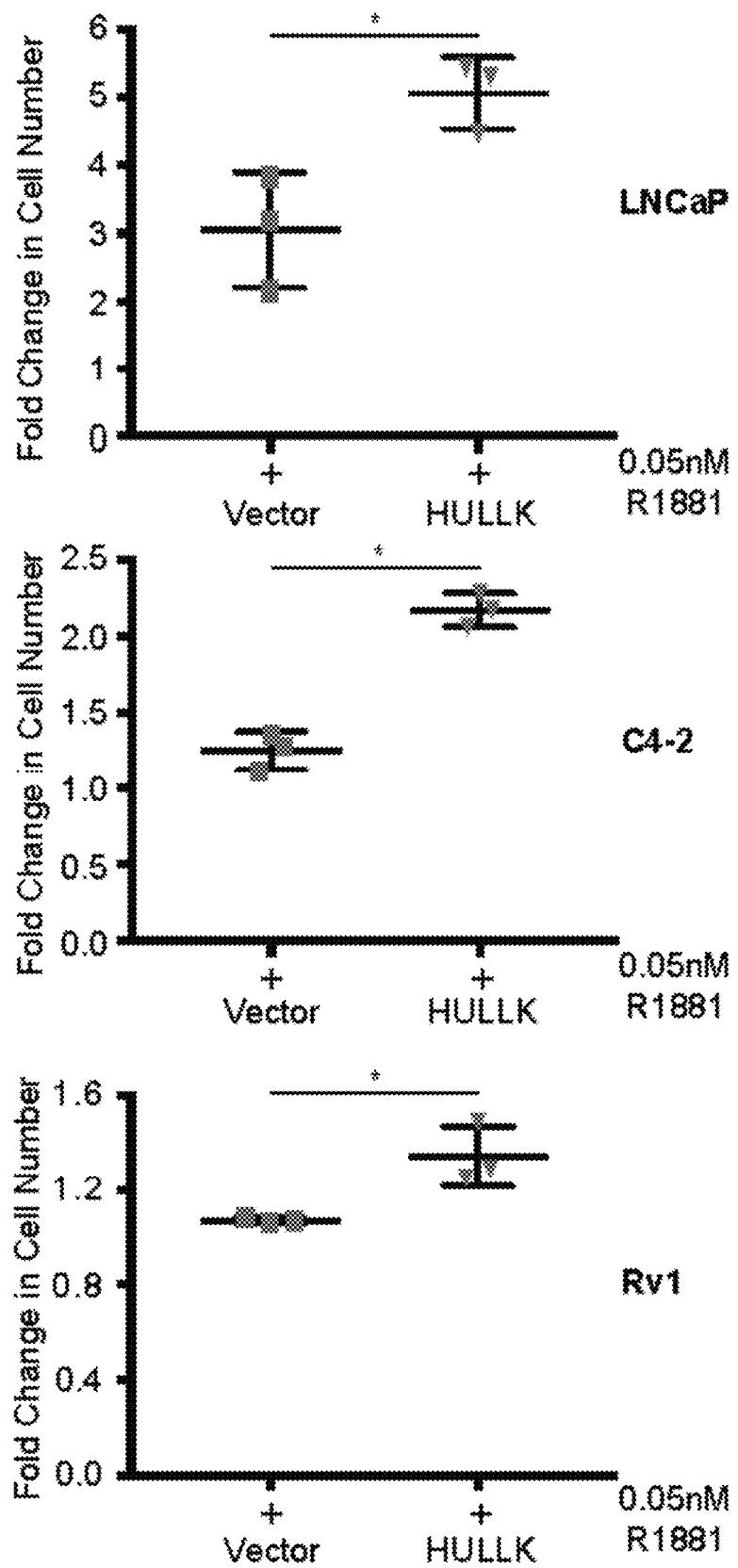

The complement experiment of evaluating the effects of overexpressing HULLK on cell growth was also performed. LNCaP, C4-2, and Rv1 cells were transduced with lentivirus expressing either vector or HULLK constructs in the presence or absence of 0.05 nM R1881, and proliferation was calculated seven days following viral transduction. Overexpression of HULLK did not provide a growth advantage over vector-expressing cells in androgen-deprived media (data not shown). The expected increase in cell growth in all vector-expressing control cells exposed to R1881 (FIG. 5D) was observed. However, hormone significantly increased proliferation in HULLK-overexpressing cells compared to vector control cells, suggesting that there may be a greater sensitivity to hormone when HULLK is overexpressed in PCa cells. Together, these data indicate that HULLK is a positive regulator of PCa cell growth and may help drive CRPC by increasing sensitivity to hormone.

Example 6

Discussion of Experimental Results

One in forty-one men diagnosed with PCa will die from the disease. While ADT is the current initial treatment for advanced PCa, eventually all men diagnosed with PCa will develop incurable CRPC. Therefore, there exists a serious need for more effective therapies for the treatment of advanced PCa, and that requires a more complete understanding of PCa development and progression. Described herein is a previously unannotated lncRNA, referred to as HULLK for Hormone Upregulated lncRNA within LCK, that functions as a positive regulator of PCa cells and the expression of which correlates with high grade PCa.

Genome sequencing has led to the surprising discovery that protein-coding RNAs only make up approximately 2% of the human genome, while ncRNAs represents 70-90% (34). Once believed to be transcriptional noise, ncRNAs are now associated with many normal biological processes, including transcriptional and translational regulation, chromatin modification, and cell cycle regulation. Furthermore, accumulating evidence supports vital roles in cancer initiation, development, and progression for ncRNAs (35,36), which are generically divided into two groups: small and long noncoding transcripts. While small ncRNAs, especially microRNAs, have been well-documented to play important roles in human disease by regulating the expression of target mRNA, lncRNAs are only beginning to be investigated and scrutinized. Even though thousands of lncRNAs have been annotated in the human genome, few functional lncRNAs in PCa have been fully characterized.

Disclosed herein is a novel lncRNA in PCa from a high-throughput RNAi screen to uncover potential regulators of PCa cell growth. LCK was identified from the shRNA screen as a positive regulator of PCa cellular proliferation. However, LCK protein expression was never detected. Immunoprecipitation and Western analyses revealed that LCK could only be observed in control Jurkat cells and not LNCaP or C4-2 PCa cell lines. The inability to recognize LCK in PCa cells was not due to the short LCK half-life, as the proteasome inhibitor MG132 did not facilitate the detection of LCK protein. The open reading frame (ORF) finder from the National Center for Biotechnology Information predicted that there were one long and two short ORFs in the HULLK sequence. According to the GenScript Codon Bias tool, the two short ORFs have low codon adaptation indices (CAI) (<0.8), suggesting poor expression. The long ORF, which is in frame with LCK and corresponds to the kinase domain, has a CAI (0.83) similar to LCK exons 1-5, suggesting that this ORF calculated to produce a 28.59 kDa protein has an equal chance of being expressed as exons 1-5 of LCK. Furthermore, data from the FANTOM Project suggested that there was a TSS near LCK exon 12, resulting in an estimated 13 kDa truncated LCK protein (39). Using an antibody raised against tyrosine 505 in exon 13 (kinase domain) of human LCK, the predicted 28.59 kDa or 13 kDa LCK protein or any other shorter LCK isoforms were able to be detected. This antibody did recognize LCK in Jurkat cells. These data suggested that LCK protein was not expressed in PCa cells. The disclosed data are consistent with the ChIP-seq dataset from the ENCODE Project, where the H3K4me3 peaks were highly enriched at active promoters near TSSs in Jurkat cells (40). Therefore, the shRNAs utilized in the kinome screen may have targeted a noncoding RNA within the LCK gene locus.

5'/3' RACE was utilized to uncover a novel noncoding transcript that aligned with the LCK gene and completely overlapped exons 6-13 and 3'UTR on the sense strand of DNA. All of the clones examined from the 3' RACE showed the same end, but several clones from the 5' RACE varied in the ends by roughly 5-20 nucleotides. The presence of a 5'-3' exoribonuclease in the PCR reaction likely account for these differences in 5' ends.

Ning and colleagues reanalyzed the dataset from the Necsulea et al study (41) and reported that 29.3% of 24,793 annotated lncRNAs overlapped protein-coding genes (42). The overlapping lncRNAs were categorized into five main groups based on DNA strand: overlapping on opposite strands (5'-regions overlap, 3'-regions overlap, embedded pairs) and overlapping on same strand (5'-regions overlap with 3'-regions, embedded pairs). The embedded pairs on either strand represented 76.4% of all annotated overlapping lncRNA-protein-coding pairs. The majority of the overlaps (~93%) occurred on the opposite DNA strand. However, lncRNAs embedded in a protein-coding gene on the same DNA strand only amounted to 5.6%. Similar to the fact that overlapping genes tend to be coexpressed (43), lncRNA-protein-coding pairs exhibited an overall positive expression correlation, with the Spearman coefficient for same strand overlaps being greater than opposite strand overlaps (42). These observations suggested that the HULLK-LCK gene pair may be rare, since they overlapped on the same strand and the protein-coding partner is not expressed in PCa cells.

The cellular compartment in which a particular lncRNA is localized may be used as a cue to its functions. Nuclear lncRNAs can facilitate epigenetic regulation through the binding of chromatin and chromatin modifying proteins (44), whereas cytoplasmic lncRNAs can influence several cellular processes, including protein degradation and transcription (45). Much less is known about cytoplasmic lncRNAs compared to their nuclear counterparts. The disclosed work on HULLK augments the growing list of cytoplasmic lncRNA functions. The functional role of HULLK in PCa was explored by knocking down HULLK with two independent shRNAs in LNCaP, C4-2, and Rv1 cells. There was a significant decrease in cell growth in the absence and presence of androgens when HULLK was depleted from the cell. HULLK overexpression resulted in a modest but consistent increase in cellular proliferation in response to hormone. These results suggested that HULLK is oncogenic in nature, similar to other lncRNAs in PCa, including PCAT-1 (45), PCA3 (3), and SChLAP1 (46).

Figure 7A:
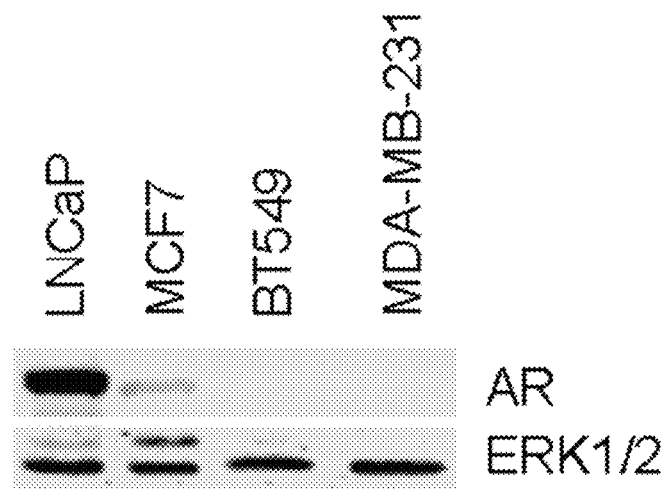
FIGS. 7A and 7B illustrate the regulation of HULLK by the AR in breast cancer cells.
Figure 7B:
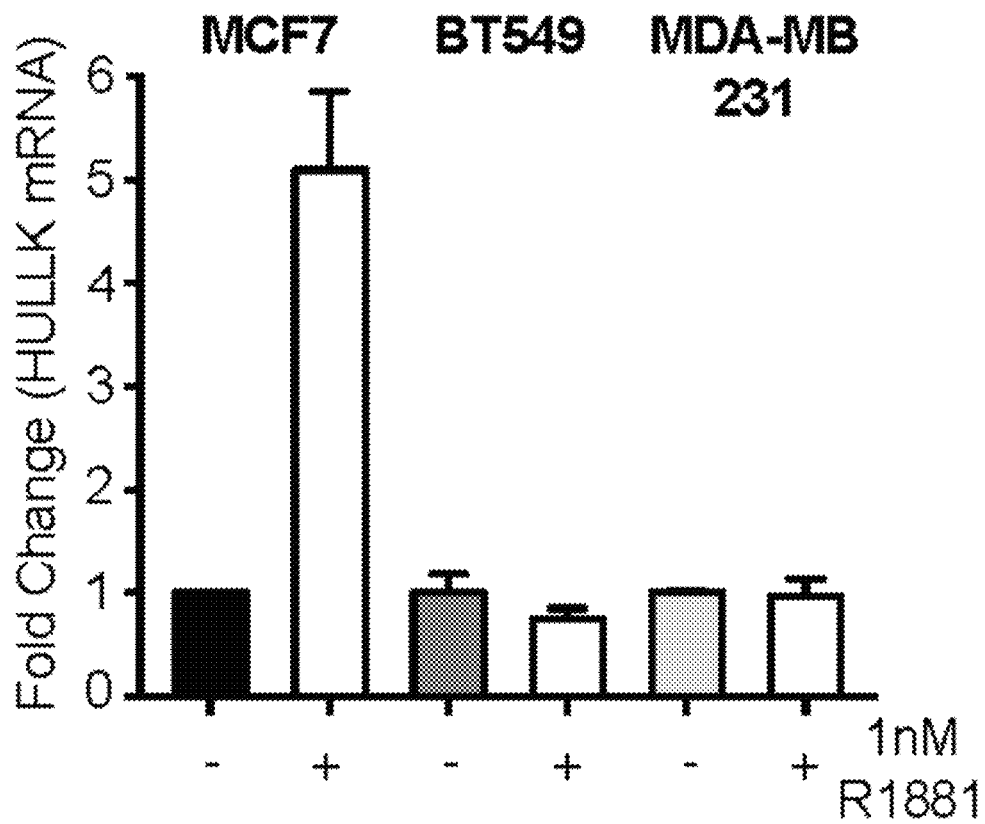

The expression of lncRNAs typically has been cell-type and tissue specific (1). Furthermore, lncRNAs that overlap protein-coding genes showed higher tissue specificity than non-overlapping lncRNA-protein-coding gene pairs (42). The data disclosed herein were mainly consistent with the tissue specificity of lncRNAs, including observation of HULLK expression in a panel of PCa cell lines and tissue. HULLK transcripts were not quantitated above transcriptional noise in cervical or pancreatic cancer cell lines. However, HULLK transcripts were discovered in MCF7 cells and not BT549 or MDA-MB-231 cells. While all three of the BCa lines are reported to express AR (47,48), in these laboratory tests only AR protein levels are only detected in MCF7 and not BT549 or MDB-MB-231 cells (FIG. 7A). Furthermore, HULLK expression increases in response to 1 nM R1881 in MCF7 cells, but not BT549 or MDA-MB-231 cells (FIG. 7B). In addition to the prostate specificity of HULLK, these data also suggest that HULLK may be expressed in other tissues where AR is active. Akin to PCGEM1 (49), CTBP1-AS (11), and PCA3 (3) lncRNAs, HULLK was upregulated in response to androgen. More importantly, expression of HULLK was significantly upregulated in high-grade PCa specimens in three cohorts, including the PCa TCGA.

Since LCK-expressing lymphocytes infiltrate prostate tumors (50), the fact that HULLK lacked LCK exons 1-5 was exploited, and the ratio of c-terminal LCK primers:n-terminal primers (HULLK:FL-LCK) was used to distinguish HULLK expression from LCK. It was observed that the ratios for the FFPE samples were higher than the fresh frozen tissue. These ratios could be influenced by differences in tissue collection and composition. For the FFPEs, the extent of infiltrating lymphocyte contamination was reduced by demarcating portions of tumor from surrounding lymphocyte-containing stroma. Decreasing the stromal contribution would diminish the amount of LCK, and thus, increase the ratios of HULLK:LCK. Even with the compounded presence of lymphocytes in the fresh frozen cohort, HULLK expression still displayed a significant upregulation with increasing Gleason score. Examining the TCGA data for the 3'/5' ratio of LCK validated this observation, which showed increasing HULLK expression in tumor compared to normal, and within tumors, with higher Gleason score compared to low Gleason score. The same finding of HULLK expression correlating with Gleason score in three independent cohorts, when considered with the experimental data that HULLK over expression increases growth and HULLK knockdown decreases PCa growth in androgen-dependent and castration-resistant PCa lines, strongly suggests that HULLK expression is associated with aggressive disease and may be a driver of PCa.

As disclosed herein, a potential mechanism for growth stimulation by HULLK was explored. Since HULLK is embedded in the LCK gene locus, it was first hypothesized that HULLK may be regulating cell growth through the modulation of the expression of Src family kinases. Knockdown of HULLK with shRNAs revealed that the levels of protein and message of each Src family member examined (Blk, Fgr, Frk, Fyn, Hck, Lyn, Src, and Yes) were not significantly altered, suggesting that HULLK may not affect cell proliferation through the regulation of Src family kinase expression (data not shown).

lncRNAs can exert their effects locally by regulating the expression of neighboring genes in cis or distantly in trans (51). There are two genes immediately 5' (Eukaryotic translation initiation factor 3 subunit I, EIF3I) and 3' (histone deacetylase 1, HDAC1) of HULLK with reported biological functions that may influence cell growth. EIF3I plays a crucial role in the initiation of protein synthesis, whereas HDAC1 interacts with the retinoblastoma tumor-suppressor protein to control cell proliferation and differentiation (52). To determine whether the effects on cell growth mediated by HULLK were a result of the regulation of gene expression in cis, the transcript levels of EIF3I and HDAC1 were measured in HULLK-depleted PCa cells. It was found that HULLK knockdown did not dramatically change the amounts of message of either gene, suggesting that the regulation of gene expression in cis, at least for these two genes, may not account for the HULLK-mediated effects on cell growth (data not shown). While no significant alterations in these genes at the RNA level was observed, the possibility that HULLK may be affecting these genes at the protein level cannot be ruled out. lncRNAs can function as scaffolds or sponges, thereby influencing translation efficiency, cellular localization, or protein stability (51).

Example 7

Conclusions

Disclosed herein is a novel lncRNA completely overlapping exons 6-13 and 3'UTR of the LCK gene on 1p35.1. The data disclosed herein establish that this lncRNA is regulated by androgens and the AR, and as such, this lncRNA has been named "HULLK" for Hormone Upregulated lncRNA within LCK. The instant disclosure reveals that HULLK is localized to the cytoplasm and found on the sense strand within the LCK gene. HULLK is expressed in PCa cell lines and upregulated as PCa progresses to metastatic disease. As demonstrated herein, HULLK functions as an oncogene to positively regulate PCa cell proliferation. Thus, the data herein enhances the understanding of lncRNA biology and may assist in the development of additional biomarkers or more effective therapeutic targets for advanced PCa.

REFERENCES

All references listed herein including but not limited to all patents, patent applications and publications thereof, scientific journal articles, and database entries (e.g., GENBANK® database entries and all annotations available therein) are incorporated herein by reference in their entireties to the extent that they supplement, explain, provide a background for, or teach methodology, techniques, and/or compositions employed herein.

1. Prensner J R, Chinnaiyan A M. The emergence of lncRNAs in cancer biology. Cancer Discov [Internet]. 2011 October; 1(5):391-407.
2. Xu S, Yi X-M, Tang C-P, Ge J-P, Zhang Z-Y, Zhou W-Q. Long non-coding RNA ATB promotes growth and epithelial-mesenchymal transition and predicts poor prognosis in human prostate carcinoma. Oncol Rep [Internet]. 2016 May 9 [cited 2017 Jul. 3]; 36(1):10-22.
3. Lemos AEG, Ferreira L B, Batoreu N M, de Freitas P P, Bonamino M H, Gimba ERP. PCA3 long noncoding RNA modulates the expression of key cancer-related genes in LNCaP prostate cancer cells. Tumor Biol [Internet]. 2016 Aug. 9 [cited 2017 Jul. 3]; 37(8):11339-48.
4. Salameh A, Lee A K, Card?-Vila M, Nunes D N, Efstathiou E, Staquicini F I, et al. PRUNE2 is a human prostate cancer suppressor regulated by the intronic long noncoding RNA PCA3. Proc Natl Acad Sci [Internet]. 2015 Jul. 7 [cited 2017 Jul. 5]; 112(27):8403-8.
5. Kretz M, Webster D E, Flockhart R J, Lee C S, Zehnder A, Lopez-Pajares V, et al. Suppression of progenitor differentiation requires the long noncoding RNA ANCR. Genes Dev [Internet]. 2012 Feb. 15 [cited 2017 Jul. 5]; 26(4):338-43.
6. Heer R, Robson C N, Shenton B K, Leung H Y. The role of androgen in determining differentiation and regulation of androgen receptor expression in the human prostatic epithelium transient amplifying population. J Cell Physiol [Internet]. 2007 September [cited 2017 Jul. 5]; 212(3): 572-8.
7. Ma W-L, Jeng L-B, Lai H-C, Liao P-Y, Chang C. Androgen receptor enhances cell adhesion and decreases cell migration via modulating β1-integrin-AKT signaling in hepatocellular carcinoma cells. Cancer Lett [Internet]. 2014 Aug. 28 [cited 2017 Jul. 5]; 351(1):64-71.
8. Jia J, Li F, Tang X-S, Xu S, Gao Y, Shi Q, et al. Long noncoding RNA DANCR promotes invasion of prostate cancer through epigenetically silencing expression of TIMP2/3. Oncotarget [Internet]. 2014 Nov. 9 [cited 2017 Jul. 5]; 7(25):37868-81.
9. Malik R, Patel L, Prensner J R, Shi Y, Iyer M K, Subramaniyan S, et al. The lncRNA PCAT29 Inhibits Oncogenic Phenotypes in Prostate Cancer. Mol Cancer Res [Internet]. 2014 August [cited 2014 Aug. 28]; 12(8): 1081-7.
10. Zhang Z, Zhou N, Huang J, Ho T-T, Zhu Z, Qiu Z, et al. Regulation of androgen receptor splice variant AR3 by PCGEM1. Oncotarget [Internet]. 2016 Mar. 29 [cited 2017 Jul. 5]; 7(13):15481-91.
11. Takayama K, Horie-Inoue K, Katayama S, Suzuki T, Tsutsumi S, Ikeda K, et al. Androgen-responsive long noncoding RNA CTBP1-A S promotes prostate cancer. EMBO J [Internet]. 2013 May 3 [cited 2018 Apr. 7]; 32(12):1665-80.
12. Zhang A, Zhao J C, Kim J, Fong K, Yang Y A, Chakravarti D, et al. LncRNA HOTAIR Enhances the Androgen-Receptor-Mediated Transcriptional Program and Drives Castration-Resistant Prostate Cancer. Cell Rep [Internet]. 2015 Oct. 6 [cited 2017 Jul. 5]; 13(1):209-21.
13. Chakravarty D, Sboner A, Nair S S, Giannopoulou E, Li R, Hennig S, et al. The oestrogen receptor alpha-regulated lncRNA NEAT1 is a critical modulator of prostate cancer. Nat Commun [Internet]. 2014 Nov. 21 [cited 2018 Apr. 5]; 5:5383.
14. Ylipää A, Kivinummi K, Kohvakka A, Annala M, Latonen L, Scaravilli M, et al. Transcriptome Sequencing Reveals PCAT5 as a Novel ERG-Regulated Long Noncoding RNA in Prostate Cancer. Cancer Res [Internet]. 2015 Oct. 1 [cited 2018 Nov. 16]; 75(19):4026-31.
15. Prensner J R, Iyer M K, Sahu A, Asangani I A, Cao Q, Patel L, et al. The long noncoding RNA SChLAP1 promotes aggressive prostate cancer and antagonizes the SWI/SNF complex. Nat Genet [Internet]. 2013 November [cited 2014 Apr. 21]; 45(11):1392-8.
16. Derrien T, Johnson R, Bussotti G, Tanzer A, Djebali S, Tilgner H, et al. The GENCODE v7 catalog of human long noncoding RNAs: Analysis of their gene structure, evolution, and expression. Genome Res [Internet]. 2012 Sep. 1 [cited 2018 Nov. 15]; 22(9):1775-89.
17. Gordon V, Bhadel S, Wunderlich W, Zhang J, Ficarro S B, Mollah S A, et al. CDK9 regulates A R promoter selectivity and cell growth through serine 81 phosphorylation. Mol Endocrinol [Internet]. 2010 December [cited 2012 Mar. 13]; 24(12):2267-80.
18. Whitworth H, Bhadel S, Ivey M, Conaway M, Spencer A, Hernan R, et al. Identification of Kinases Regulating Prostate Cancer Cell Growth Using an RNAi Phenotypic Screen. PLoS One [Internet]. 2012 June [cited 2013 Sep. 11]; 7(6).
19. Hurley P J, Bunz F. ATM and ATR: components of an integrated circuit. Cell Cycle [Internet]. 2007 February; 6(4):414-7.
20. Harris K F, Shoji I, Cooper E M, Kumar S, Oda H, Howley P M. Ubiquitin-mediated degradation of active Src tyrosine kinase. Proc Natl Acad Sci USA [Internet]. 1999 Nov. 23 [cited 2017 Jun. 28]; 96(24):13738-43.
21. Oda H, Kumar S, Howley P M. Regulation of the Src family tyrosine kinase Blk through E6A P-mediated ubiquitination. Proc Natl Acad Sci USA [Internet]. 1999 Aug. 17 [cited 2017 Jun. 28]; 96(17):9557-62.
22. Rao N, Miyake S, Reddi A L, Douillard P, Ghosh A K, Dodge I L, et al. Negative regulation of Lck by Cbl ubiquitin ligase. Proc Natl Acad Sci USA [Internet]. 2002 Mar. 19 [cited 2017 Jun. 28]; 99(6):3794-9.
23. Giaccia A J, Kastan M B. The complexity of p53 modulation: emerging patterns from divergent signals. Genes Dev [Internet]. 1998 Oct. 1 [cited 2017 Jun. 28]; 12(19):2973-83.
24. Heemers H V., Tindall D J. Androgen Receptor (A R) Coregulators: A Diversity of Functions Converging on and Regulating the A R Transcriptional Complex. Endocr Rev [Internet]. 2007 December [cited 2014 Mar. 13]; 28(7):778-808.
25. Fu M, Wang C, Reutens A T, Wang J, Angeletti R H, Siconolfi-Baez L, et al. p300 and p300/cAMP-response element-binding protein-associated factor acetylate the androgen receptor at sites governing hormone-dependent transactivation. J Biol Chem [Internet]. 2000 Jul. 7 [cited 2018 Oct. 11]; 275(27):20853-60.
26. Debes J D, Tindall D J. The role of androgens and the androgen receptor in prostate cancer. Cancer Lett [Internet]. 2002 Dec. 10 [cited 2018 Oct. 11]; 187(1-2):1-7. A
27. Asangani I A, Dommeti V L, Wang X, Malik R, Cieslik M, Yang R, et al. Therapeutic targeting of BET bromodomain proteins in castration-resistant prostate cancer. Nature [Internet]. 2014 Jun. 23 [cited 2018 Oct. 11]; 510(7504):278-82.
28. van Heesch S, van Iterson M, Jacobi J, Boymans S, Essers P B, de Bruijn E, et al. Extensive localization of long noncoding RNAs to the cytosol and mono- and polyribosomal complexes. Genome Biol [Internet]. 2014 January [cited 2015 Jan. 17]; 15(1):R6.
29. Clemson C M, Hutchinson J N, Sara S A, Ensminger A W, Fox A H, Chess A, et al. An architectural role for a nuclear noncoding RNA: NEAT1 RNA is essential for the structure of paraspeckles. Mol Cell [Internet]. 2009 Mar. 27 [cited 2017 Jun. 30]; 33(6):717-26.
30. Brunner A L, Beck A H, Edris B, Sweeney R T, Zhu S X, Li R, et al. Transcriptional profiling of long non-coding RNAs and novel transcribed regions across a diverse panel of archived human cancers. [cited 2017 Jun. 30];
31. Holliday D L, Speirs V. Choosing the right cell line for breast cancer research. Breast Cancer Res [Internet]. 2011 Aug. 12 [cited 2018 Nov. 2]; 13(4):215.
32. Abeshouse A, Ahn J, Akbani R, Ally A, Amin S, Andry C D, et al. The Molecular Taxonomy of Primary Prostate Cancer. Cell [Internet]. 2015 November [cited 2019 May 9]; 163(4):1011-25.
33. Sun W, Duan T, Ye P, Chen K, Zhang G, Lai M, et al. TSVdb: a web-tool for TCGA splicing variants analysis. BMC Genomics [Internet]. 2018 May 29 [cited 2019 May 9]; 19(1):405.
34. ENCODE Project Consortium. An integrated encyclopedia of DNA elements in the human genome. Nature [Internet]. 2012 Sep. 6 [cited 2018 Apr. 2]; 489(7414): 57-74.
35. Alexander R P, Fang G, Rozowsky J, Snyder M, Gerstein M B. Annotating non-coding regions of the genome. Nat Rev Genet [Internet]. 2010 Aug. 13 [cited 2018 Apr. 1]; 11 (8): 559-71.
36. Geisler S, Coller J. RNA in unexpected places: long non-coding RNA functions in diverse cellular contexts. Nat Rev Mol Cell Biol [Internet]. 2013 Nov. 9 [cited 2018 Apr. 1]; 14(11):699-712.
37. Genomics B, Hutchinson J N, Ensminger A W, Clemson C M, Lynch C R, Lawrence J B, et al. A screen for nuclear transcripts identifies two linked noncoding RNAs associated with SC35 splicing domains. BMC Genomics [Internet]. 2007 [cited 2017 Jun. 29]; 8(8).
38. Yang L, Lin C, Jin C, Yang J C, Tanasa B, Li W, et al. lncRNA-dependent mechanisms of androgen-receptor-regulated gene activation programs. Nature [Internet]. 2013 August;
39. Lizio M, Harshbarger J, Shimoji H, Severin J, Kasukawa T, Sahin S, et al. Gateways to the FANTOM5 promoter level mammalian expression atlas. Genome Biol [Internet]. 2015 Jan. 5 [cited 2018 Apr. 2]; 16(1):22.
40. Benayoun B A, Pollina E A, Ucar D, Mahmoudi S, Karra K, Wong E D, et al. H3K4me3 Breadth Is Linked to Cell Identity and Transcriptional Consistency. Cell [Internet]. 2015 Nov. 19 [cited 2018 Nov. 15]; 163(5):1281-6.
41. Necsulea A, Soumillon M, Warnefors M, Liechti A, Daish T, Zeller U, et al. The evolution of lncRNA repertoires and expression patterns in tetrapods. Nature [Internet]. 2014 Jan. 19 [cited 2018 Apr. 4]; 505(7485): 635-40.
42. Ning Q, Li Y, Wang Z, Zhou S, Sun H, Yu G. The Evolution and Expression Pattern of Human Overlapping lncRNA and Protein-coding Gene Pairs. Sci Rep [Internet]. 2017 Dec. 27 [cited 2018 Nov. 15]; 7(1):42775.
43. Balbin O A, Malik R, Dhanasekaran S M, Prensner J R, Cao X, Wu Y-M, et al. The landscape of antisense gene expression in human cancers. Genome Res [Internet]. 2015 July [cited 2018 Apr. 6]; 25(7):1068-79.
44. Lee J T. Epigenetic Regulation by Long Noncoding RNAs. Science (80-) [Internet]. 2012 Dec. 14 [cited 2018 Nov. 16]; 338(6113):1435-9.
45. Prensner J R, Chen W, Han S, Iyer M K, Cao Q, Kothari V, et al. The long non-coding RNA PCAT-1 promotes prostate cancer cell proliferation through cMyc. Neoplasia [Internet]. 2014 November [cited 2018 Apr. 5]; 16(11): 900-8.
46. Prensner J R, Iyer M K, Sahu A, Asangani I A, Cao Q, Patel L, et al. The long noncoding RNA SChLAP1 promotes aggressive prostate cancer and antagonizes the SWI/SNF complex. Nat Genet [Internet]. 2013 [cited 2017 Jun. 29]; 11.
47. Macedo L F, Guo Z, Tilghman S L, Sabnis G J, Qiu Y, Brodie A. Role of Androgens on MCF-7 Breast Cancer Cell Growth and on the Inhibitory Effect of Letrozole. Cancer Res [Internet]. 2006 Aug. 1 [cited 2018 Nov. 2]; 66(15):7775-82.
48. Barton V N, D'Amato N C, Gordon M A, Lind H T, Spoelstra N S, Babbs B L, et al. Multiple molecular subtypes of triple-negative breast cancer critically rely on androgen receptor and respond to enzalutamide in vivo. Mol Cancer Ther [Internet]. 2015 March [cited 2018 Nov. 2]; 14(3):769-78.
49. Parolia A, Crea F, Xue H, Wang Y, Mo F, Ramnarine V, et al. The long non-coding RNA PCGEM1 is regulated by androgen receptor activity in vivo. Mol Cancer [Internet]. 2015 Feb. 21 [cited 2018 Apr. 7]; 14(1):46.
50. Rädestad E, Egevad L, Jorns C, Mattsson J, Sundberg B, Nava S, et al. Characterization of infiltrating lymphocytes in human benign and malignant prostate tissue. Oncotarget [Internet]. 2017 Sep. 1 [cited 2018 Apr. 8]; 8(36): 60257-69.
51. Akhade V S, Pal D, Kanduri C. Long Noncoding RNA: Genome Organization and Mechanism of Action. In: Advances in experimental medicine and biology [Internet]. 2017 [cited 2019 Apr. 24]. p. 47-74.
52. Magnaghi-Jaulin L, Groisman R, Naguibneva I, Robin P, Lorain S, Le Villain J P, et al. Retinoblastoma protein represses transcription by recruiting a histone deacetylase. Nature [Internet]. 1998 Feb. 5 [cited 2019 Apr. 24]; 391(6667):601-5.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method of modulating lymphocyte-specific protein tyrosine kinase (LCK) activity in a vertebrate subject, the method comprising:
   administering to the vertebrate subject an effective amount of a substance capable of modulating expression of an LCK gene in the vertebrate subject,
   wherein the substance comprises an RNA interference (RNAi) molecule directed to the LCK gene, whereby modulation of LCK activity is accomplished and whereby modulating expression of the LCK gene modulates growth and/or proliferation of a prostate cancer (PCa) cell within the vertebrate subject,
   wherein the RNAi molecule comprises a short hairpin RNA (shRNA), whereby the shRNA modulates expression of the LCK gene by RNAi, and wherein the shRNA comprises shLCK-3 and/or shLCK-4.

2. The method of claim 1, wherein modulating expression of the LCK gene comprises modulating expression of a long noncoding RNA (lncRNA) of the LCK gene.

3. The method of claim 2, wherein the lncRNA comprises a hormone upregulated lncRNA within the LCK gene (HULLK).

4. The method of claim 3, wherein HULLK comprises a nucleotide sequence having at least about 75% sequence identity to SEQ ID NO. 1.

5. The method of claim 1, wherein the shRNA is configured to target a carboxy-terminal of the LCK gene.

6. The method of claim 1, wherein the substance further comprises an anti-androgen compound.

7. The method of claim 1, wherein the substance further comprises a delivery vehicle, wherein the delivery vehicle comprises a viral vector, an antibody, an aptamer and/or a nanoparticle, for delivering the shRNA to a target cell.

8. The method of claim 1, wherein the RNAi molecule comprises a small interfering RNA (siRNA), whereby the siRNA modulates expression the LCK gene by RNAi.

9. The method of claim 8, wherein the substance further comprises a delivery vehicle, wherein the delivery vehicle is selected from a viral vector, an antibody, an aptamer, or a nanoparticle for delivering the siRNA to a target cell.

10. The method of claim 3, wherein the substance is configured to target HULLK in cytoplasm of a cell in the vertebrate subject.

11. A method of modulating lymphocyte-specific protein tyrosine kinase (LCK) activity in a vertebrate subject, the method comprising:
    administering to the vertebrate subject an effective amount of a substance capable of modulating expression of an LCK gene in the vertebrate subject and wherein the vertebrate subject is suffering from prostate cancer (PCa), wherein the PCa comprises androgen-dependent PCa and/or castration-resistant PCa,
    wherein the substance comprises an RNA interference (RNAi) molecule directed to the LCK gene, whereby modulation of LCK activity is accomplished, and
    wherein the RNAi molecule comprises a short hairpin RNA (shRNA), whereby the shRNA modulates expression of the LCK gene by RNAi, and wherein the shRNA comprises shLCK-3 and/or shLCK-4.

12. The method of claim 11, wherein modulating expression of the LCK gene comprises modulating expression of a long noncoding RNA (lncRNA) of the LCK gene.

13. The method of claim 12, wherein the lncRNA comprises a hormone upregulated lncRNA within the LCK gene (HULLK).

14. The method of claim 13, wherein HULLK comprises a nucleotide sequence having at least about 75% sequence identity to SEQ ID NO. 1.

15. The method of claim 11, wherein the shRNA is configured to target a carboxy-terminal of the LCK gene.

16. The method of claim 11, wherein the substance further comprises an anti-androgen compound.

17. The method of claim 16, wherein the anti-androgen compound is selected from the group consisting of enzalutamide, an inhibitor of p300, an inhibitor of the bromodomain family, and an inhibitor of the extra-terminal (BET) family.

18. The method of claim 11, wherein the substance further comprises a delivery vehicle, wherein the delivery vehicle comprises a viral vector, an antibody, an aptamer and/or a nanoparticle, for delivering the shRNA to a target cell.

19. The method of claim 11, wherein the RNAi molecule comprises a small interfering RNA (siRNA), whereby the siRNA modulates expression the LCK gene by RNAi.

20. The method of claim 18, wherein the substance further comprises a delivery vehicle, wherein the delivery vehicle is selected from a viral vector, an antibody, an aptamer, or a nanoparticle for delivering the siRNA to a target cell.

21. The method of claim 13, wherein the substance is configured to target HULLK in cytoplasm of a cell in the vertebrate subject.

22. The method of claim 6, wherein the anti-androgen compound is selected from the group consisting of enzalutamide, an inhibitor of p300, an inhibitor of the bromodomain family, and an inhibitor of the extra-terminal (BET) family.

* * * * *

SEQUENCE LISTING

```
<160> NUMBER OF SEQ ID NOS: 26

<210> SEQ ID NO 1
<211> LENGTH: 1694
<212> TYPE: DNA
<213> ORGANISM: Homo sapiens

<400> SEQUENCE: 1
ctggttcttc aagaacctga gccgcaagga cgcggagcgg cagctcctgg cgcccgggaa      60
cactcacggc tccttcctca tccgggagag cgagagcacc gcgggtgagc gggcggcggt     120
```

```
ctcgaccggg cgcggggtg ccccggggtg tgcccgaggg ggggcgcagg gtgagcccga      180
ggtggagaca cggggatcgt tttcactgtc ggtccgggac ttcgaccaga accagggaga      240
ggtggtgaaa cattacaaga tccgtaatct ggacaacggt ggcttctaca tctcccctcg      300
aatcactttt cccggcctgc atgaactggt ccgccattac accatgcttc agatgggct      360 gtgcacacgg ttgagccgcc cctgccagac ccagaagccc cagaagccgt ggtgggagga      420
cgagtgggag gttcccaggg agacgctgaa gctggtggag cggctggggg ctggacagtt      480
cggggaggtg tggatggggt actacaacgg gcacacgaag gtggcggtga agagcctgaa      540
gcagggcagc atgtccccgg acgccttcct ggccgaggcc aacctcatga agcagctgca      600
acaccagcgg ctggttcggc tctacgctgt ggtcacccag gagcccatct acatcatcac      660
tgaatacatg gagaatggga gtctagtgga ttttctcaag accccttcag gcatcaagtt      720
gaccatcaac aaactcctgg acatggcagc ccaaattgca gaaggcatgg cattcattga      780
agagcggaat tatattcatc gtgaccttcg ggctgccaac attctggtgt ctgacaccct      840
gagctgcaag attgcagact ttggcctagc acgcctcatt gaggacaacg agtacacagc      900
cagggagggg gccaagtttc ccattaagtg gacagcgcca aagccatta actacgggac      960 attcaccatc aagtcagatg tgtggtcttt tgggatcctg ctgacggaaa ttgtcaccca     1020
cggccgcatc ccttacccag ggatgaccaa cccggaggtg attcagaacc tggagcgagg     1080
ctaccgcatg gtgcgccctg acaactgtcc agaggagctg taccaactca tgaggctgtg     1140
ctggaaggag cgcccagagg accggccac ctttgactac ctgcgcagtg tgctggagga     1200
cttcttcacg gccacagagg gccagtacca gcctcagcct tgagaggcct tgagaggccc     1260
tggggttctc cccctttctc tccagcctga cttggggaga tggagttctt gtgccatagt     1320
cacatggcct atgcacatat ggactctgca catgaatccc acccacatgt gacacatatg     1380
caccttgtgt ctgtacacgt gtcctgtagt tgcgtggact ctgcacatgt cttgtacatg     1440
tgtagcctgt gcatgtatgt cttggacact gtacaaggta ccccttctg gctctcccat     1500 ttcctgagac cacagagaga ggggagaagc ctgggattga cagaagcttc tgcccaccta     1560 cttttcttc ctcagatcat ccagaagttc tcaagggcc aggactttat ctaataccte     1620 tgtgtgctcc tccttggtgc ctggcctggc acacatcagg agttcaataa atgtctgttg     1680
atgactgttg taca                                                      1694

<210> SEQ ID NO 2
<211> LENGTH: 52
<212> TYPE: DNA
<213> ORGANISM: Artificial Sequence
<220> FEATURE:
<223> OTHER INFORMATION: Artificially synthesized oligonucleotide primer

<400> SEQUENCE: 2
ggggacaagt ttgtacaaaa aagcaggctt cctggttctt caagaacctg ag             52

<210> SEQ ID NO 3
<211> LENGTH: 71
<212> TYPE: DNA
<213> ORGANISM: Artificial Sequence
<220> FEATURE:
<223> OTHER INFORMATION: Artificially synthesized oligonucleotide primer

<400> SEQUENCE: 3
ggggacaagt ttgtacaaaa aagcaggctt cgaaggagat agaaccatgg ctggttcttc      60
aagaacctga g                                                          71
```

<210> SEQ ID NO 4
<211> LENGTH: 55
<212> TYPE: DNA
<213> ORGANISM: Artificial Sequence
<220> FEATURE:
<223> OTHER INFORMATION: Artificially synthesized oligonucleotide primer

<400> SEQUENCE: 4
ggggaccact tgtacaaga aagctgggtc tcatcaacag acatttattg aactc    55

<210> SEQ ID NO 5
<211> LENGTH: 58
<212> TYPE: DNA
<213> ORGANISM: Artificial Sequence
<220> FEATURE:
<223> OTHER INFORMATION: Artificially synthesized oligonucleotide primer

<400> SEQUENCE: 5
ggggaccact tgtacaaga aagctgggtc ctatcatcaa cagacattta ttgaactc    58

<210> SEQ ID NO 6
<211> LENGTH: 21
<212> TYPE: DNA
<213> ORGANISM: Artificial Sequence
<220> FEATURE:
<223> OTHER INFORMATION: Artificially synthesized oligonucleotide primer

<400> SEQUENCE: 6
cttcgtgtgc ccgttgtagt a    21

<210> SEQ ID NO 7
<211> LENGTH: 21
<212> TYPE: DNA
<213> ORGANISM: Artificial Sequence
<220> FEATURE:
<223> OTHER INFORMATION: Artificially synthesized oligonucleotide primer

<400> SEQUENCE: 7
cccgaaggtc acgatgaata t    21

<210> SEQ ID NO 8
<211> LENGTH: 21
<212> TYPE: DNA
<213> ORGANISM: Artificial Sequence
<220> FEATURE:
<223> OTHER INFORMATION: Artificially synthesized oligonucleotide primer

<400> SEQUENCE: 8
taccaactca tgaggctgtg c    21

<210> SEQ ID NO 9
<211> LENGTH: 22
<212> TYPE: DNA
<213> ORGANISM: Artificial Sequence
<220> FEATURE:
<223> OTHER INFORMATION: Artificially synthesized oligonucleotide primer

<400> SEQUENCE: 9
cagacattta ttgaactcct ga    22

<210> SEQ ID NO 10
<211> LENGTH: 18
<212> TYPE: DNA
<213> ORGANISM: Artificial Sequence
<220> FEATURE:

<223> OTHER INFORMATION: Artificially synthesized oligonucleotide primer

<400> SEQUENCE: 10
atcgttttca ctgtcggt         18

<210> SEQ ID NO 11
<211> LENGTH: 20
<212> TYPE: DNA
<213> ORGANISM: Artificial Sequence
<220> FEATURE:
<223> OTHER INFORMATION: Artificially synthesized oligonucleotide primer

<400> SEQUENCE: 11
gtgtgagaac tgccattatc         20

<210> SEQ ID NO 12
<211> LENGTH: 18
<212> TYPE: DNA
<213> ORGANISM: Artificial Sequence
<220> FEATURE:
<223> OTHER INFORMATION: Artificially synthesized oligonucleotide primer

<400> SEQUENCE: 12
agagccattt cggatgag         18

<210> SEQ ID NO 13
<211> LENGTH: 18
<212> TYPE: DNA
<213> ORGANISM: Artificial Sequence
<220> FEATURE:
<223> OTHER INFORMATION: Artificially synthesized oligonucleotide primer

<400> SEQUENCE: 13
caacctggtt atcgctct         18

<210> SEQ ID NO 14
<211> LENGTH: 18
<212> TYPE: DNA
<213> ORGANISM: Artificial Sequence
<220> FEATURE:
<223> OTHER INFORMATION: Artificially synthesized oligonucleotide primer

<400> SEQUENCE: 14
ccttctcaaa gcccagat         18

<210> SEQ ID NO 15
<211> LENGTH: 19
<212> TYPE: DNA
<213> ORGANISM: Artificial Sequence
<220> FEATURE:
<223> OTHER INFORMATION: Artificially synthesized oligonucleotide primer

<400> SEQUENCE: 15
atggcattca ttgaagagc         19

<210> SEQ ID NO 16
<211> LENGTH: 19
<212> TYPE: DNA
<213> ORGANISM: Artificial Sequence
<220> FEATURE:
<223> OTHER INFORMATION: Artificially synthesized oligonucleotide primer

<400> SEQUENCE: 16
gtcagacacc agaatgttg         19

```
<210> SEQ ID NO 17
<211> LENGTH: 18
<212> TYPE: DNA
<213> ORGANISM: Artificial Sequence
<220> FEATURE:
<223> OTHER INFORMATION: Artificially synthesized oligonucleotide primer

<400> SEQUENCE: 17
ggagctgtac caactcat                                                  18

<210> SEQ ID NO 18
<211> LENGTH: 18
<212> TYPE: DNA
<213> ORGANISM: Artificial Sequence
<220> FEATURE:
<223> OTHER INFORMATION: Artificially synthesized oligonucleotide primer

<400> SEQUENCE: 18
caggtagtca aaggtggg                                                  18

<210> SEQ ID NO 19
<211> LENGTH: 18
<212> TYPE: DNA
<213> ORGANISM: Artificial Sequence
<220> FEATURE:
<223> OTHER INFORMATION: Artificially synthesized oligonucleotide primer

<400> SEQUENCE: 19
atccagaagt tcctcaag                                                  18

<210> SEQ ID NO 20
<211> LENGTH: 19
<212> TYPE: DNA
<213> ORGANISM: Artificial Sequence
<220> FEATURE:
<223> OTHER INFORMATION: Artificially synthesized oligonucleotide primer

<400> SEQUENCE: 20
ttacaacagt catcaacag                                                 19

<210> SEQ ID NO 21
<211> LENGTH: 18
<212> TYPE: DNA
<213> ORGANISM: Artificial Sequence
<220> FEATURE:
<223> OTHER INFORMATION: Artificially synthesized oligonucleotide primer

<400> SEQUENCE: 21
cggaggtgga ttctgtta                                                  18

<210> SEQ ID NO 22
<211> LENGTH: 18
<212> TYPE: DNA
<213> ORGANISM: Artificial Sequence
<220> FEATURE:
<223> OTHER INFORMATION: Artificially synthesized oligonucleotide primer

<400> SEQUENCE: 22
gtgtagcaag tctggtga                                                  18

<210> SEQ ID NO 23
<211> LENGTH: 18
<212> TYPE: DNA
<213> ORGANISM: Artificial Sequence
<220> FEATURE:
<223> OTHER INFORMATION: Artificially synthesized oligonucleotide primer
```

```
<400> SEQUENCE: 23
ggtctgagga gtgatgtg                                                        18

<210> SEQ ID NO 24
<211> LENGTH: 18
<212> TYPE: DNA
<213> ORGANISM: Artificial Sequence
<220> FEATURE:
<223> OTHER INFORMATION: Artificially synthesized oligonucleotide primer

<400> SEQUENCE: 24
aagcgttggt caatgttg                                                        18

<210> SEQ ID NO 25
<211> LENGTH: 58
<212> TYPE: DNA
<213> ORGANISM: Artificial Sequence
<220> FEATURE:
<223> OTHER INFORMATION: Artificially synthesized oligonucleotide

<400> SEQUENCE: 25 ccggggatc ctgctgacgg aaattctcga gaatttccgt cagcaggatc ccttttg              58

<210> SEQ ID NO 26
<211> LENGTH: 58
<212> TYPE: DNA
<213> ORGANISM: Artificial Sequence
<220> FEATURE:
<223> OTHER INFORMATION: Artificially synthesized oligonucleotide

<400> SEQUENCE: 26
ccggtcacat ggcctatgca catatctcga gatatgtgca taggccatgt gattttg             58
```